United States Patent
Tzianabos et al.

(10) Patent No.: US 7,083,777 B1
(45) Date of Patent: Aug. 1, 2006

(54) IMMUNOMODULATING POLYMERS

(75) Inventors: Arthur O. Tzianabos, Reading, MA (US); Dennis L. Kasper, Charlestown, MA (US); Andrew B. Onderdonk, Westwood, MA (US); Ying Wang, Brookline, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 0 days.

(21) Appl. No.: 09/540,024

(22) Filed: Mar. 31, 2000

Related U.S. Application Data

(60) Provisional application No. 60/162,457, filed on Oct. 29, 1999, provisional application No. 60/127,584, filed on Apr. 2, 1999.

(51) Int. Cl.
*A61K 38/16* (2006.01)
*A61K 38/20* (2006.01)

(52) U.S. Cl. ............... 424/9.322; 424/192.1; 530/300; 530/350; 530/378.3; 530/33; 530/402; 514/2

(58) Field of Classification Search ............ 526/72; 530/300, 350, 402, 333, 334, 378.3, 33; 514/2; 424/9.322, 193.1, 192.1
See application file for complete search history.

(56) References Cited

U.S. PATENT DOCUMENTS

| | | | |
|---|---|---|---|
| 3,849,550 A | 11/1974 | Teitelbaum et al. | 424/78 |
| 4,619,995 A | 10/1986 | Hayes | 536/20 |
| 4,819,617 A | 4/1989 | Goldberg et al. | 128/897 |
| 4,886,787 A | 12/1989 | de Belder et al. | 514/57 |
| 4,937,270 A | 6/1990 | Hamilton et al. | 514/7.1 |
| 5,130,417 A * | 7/1992 | Stanley et al. | 530/350 |
| 5,140,016 A | 8/1992 | Goldberg et al. | 514/57 |
| 5,196,510 A * | 3/1993 | Rodwell et al. | 530/324 |
| 5,215,896 A | 6/1993 | Keck et al. | 435/69.7 |
| 5,514,581 A * | 5/1996 | Ferrari et al. | 435/252.3 |
| 5,605,938 A | 2/1997 | Roufa et al. | 514/59 |
| 5,679,654 A | 10/1997 | Tzianabos et al. | 514/54 |
| 5,679,658 A | 10/1997 | Elson | 514/55 |
| 5,700,787 A | 12/1997 | Tzianabos et al. | 514/54 |
| 5,700,906 A * | 12/1997 | Arnot et al. | 530/324 |
| 5,705,178 A | 1/1998 | Roufa et al. | 424/422 |
| 5,760,200 A | 6/1998 | Miller et al. | 536/21 |
| 6,150,459 A * | 11/2000 | Mayes et al. | 525/54.1 |
| 6,447,765 B1 * | 9/2002 | Horwitz | 424/85.1 |

FOREIGN PATENT DOCUMENTS

| | | |
|---|---|---|
| DE | 3704389 A1 | 8/1988 |
| WO | WO 95/31990 | 11/1995 |
| WO | WO 96/07427 | 3/1996 |
| WO | WO 96/32119 | 10/1996 |

OTHER PUBLICATIONS

Basu, S. et al. (1997) "synthesis and characterization of a peptide nucleic acid conjugated to a D-peptide analog of insulin-like growth factor 1 for increased cellar uptake" Bioconj. Chem. vol. 8, pp. 481-488.*
Simmons, C. G. et al. (1997) "Synthesis and membrane premerbility of PNA-peptide conjugates" Biorg. Med. Chem. Lett. vol. 7, pp. 3001-3005.*
Nielsen, P. (1999) "Applications of peptide nucleic acids" Curr. Opin. Biotechnol. vol. 10, pp. 71-75.*
Bazan, J. F. (1992) Unraveling the structure of IL-2. Science. vol. 257, pp. :410-413.*
http://www.mindfully.org/Plastic/Polymers/Polyethylene-Glycols-PEGs.htm.*
Perumal VK et al., *Clinical Research* 38(2):550A (1990).
Kalka-Moll WM et al., *Abstracts of the 98th Gen. Mtg. of the Amer. Soc. for Microbiol.* 98:123 (1998).
Tzianabos A et al., *Abstracts of the 99th Gen. Mtg. of the Amer. Soc. for Microbiol.* 99:37-38 (1999).
PCT International Search Report for PCT/US00/08586.
Aharoni R et al., Bystander suppression of experimental autoimmune encephalomyelitis by T cell lines and clones of the Th2 type induced by copolymer 1. *J Neuroimmunol* Nov. 2, 1998;91(1-2):135-46.
Aharoni R et al., Copolymer 1 induces T cells of the T helper type 2 that crossreact with myelin basic protein and suppress experimental autoimmune encephalomyelitis. *Proc Natl Acad Sci U S A* Sep. 30, 1997;94(20):10821-6.
Aharoni R et al., Studies on the mechanism and specificity of the effect of the synthetic random copolymer GLAT on graft-versus-host disease. *Immunol Lett* Jul. 1997;58(2):79-87.

(Continued)

*Primary Examiner*—Jon Weber
*Assistant Examiner*—Samuel Wei Liu
(74) *Attorney, Agent, or Firm*—Wolf, Greenfield & Sacks, P.C.

(57) ABSTRACT

A pharmaceutical composition consisting of identical repeating units, each unit having a charge motif composed of a positively charged free amino moiety and a negatively charged moiety, wherein the positively charged free amino moiety and the negatively charged moiety of each charge motif are separated by at least one neutral amino acid, and wherein the positively charged free amino moiety of one of the charge motifs is separated by a distance of at least 8 amino acids from the positively charged amino moiety of another charge motif, and a pharmaceutically acceptable carrier. Said pharmaceutical composition is useful for inducing IL-2, activating T cells to produce a T helper 1 cytokine profile, suppressing IgG antibody response to specific antigen, promoting allograft survival, reducing postoperative surgical adhesion formation, and/or protecting against abscess formation associated with surgery, trauma or diseases that predispose the host to abscess formation.

7 Claims, 10 Drawing Sheets

OTHER PUBLICATIONS

Arnon R et al., New insights into the mechanism of action of copolymer 1 in experimental allergic encephalomyelitis and multiple sclerosis. *J Neurol* Apr. 1996;243(4 Suppl 1):S8-13.

Baumann H et al., Structural elucidation of two capsular polysaccharides from one strain of *Bacteroides fragilis* using high-resolution NMR spectroscopy. *Biochemistry* Apr. 28, 1992;31(16):4081-9.

Fridkis-Hareli M et al., Binding motifs of copolymer 1 to multiple sclerosis- and rheumatoid arthritis-associated HLA-DR molecules. *J Immunol* Apr. 15, 1999;162(8):4697-704.

Fridkis-Hareli M et al., Binding of random copolymers of three amino acids to class II MHC molecules. *Int Immunol* May 1999;11(5):635-41.

Fridkis-Hareli M et al., Direct binding of myelin basic protein and synthetic copolymer 1 to class II major histocompatibility complex molecules on living antigen-presenting cells—specificity and promiscuity. *Proc Natl Acad Sci U S A* May 24, 1994;91(11):4872-6.

Fridkis-Hareli M et al., Synthetic copolymer 1 and myelin basic protein do not require processing prior to binding to class II major histocompatibility complex molecules on living antigen-presenting cells. *Cell Immunol* Jul. 1995;163(2):229-36.

Gibson FC 3rd et al., Cellular mechanism of intraabdominal abscess formation by *Bacteroides fragilis*. *J Immunol* May 15, 1998;160(10):5000-6.

Gibson FC 3rd et al., The capsular polysaccharide complex of *Bacteroides fragilis* induces cytokine production from human and murine phagocytic cells. *Infect Immun* Mar. 1996;64(3):1065-9.

Kalka-Moll WM et al., Effect of molecular size on the ability of zwitterionic polysaccharides to stimulate cellular immunity. *J Immunol* Jan. 15, 2000;164(2):719-24.

Kato T et al., Interleukin 10 reduces mortality from severe peritonitis in mice. *Antimicrob Agents Chemother* Jun. 1995;39(6):1336-40.

Kennedy R et al., Prevention of experimental postoperative peritoneal adhesions by N,O-carboxymethyl chitosan. *Surgery* Nov. 1996;120(5):866-70.

Krause TJ et al., An inhibitor of cell proliferation associated with adhesion formation is suppressed by N,O-carboxymethyl chitosan. *J Invest Surg* Mar.-Apr. 1998;11(2):105-13.

Montz FJ et al., Interleukin-10: ability to minimize postoperative intraperitoneal adhesion formation in a murine model. *Fertil Steril* Jun. 1994;61(6):1136-40.

Pantosti A et al., *Bacteroides fragilis* strains express multiple capsular polysaccharides. *J Clin Microbiol* Jul. 1993;31(7):1850-5.

Pantosti A et al., Immunochemical characterization of two surface polysaccharides of *Bacteroides fragilis*. *Infect Immun* Jun. 1991;59(6):2075-82.

Pavliak V et al., Structural elucidation of the capsular polysaccharide of *Bacteroides fragilis* strain 23745M1. *Carbohydr Res* Oct. 2, 1995;275(2):333-41.

Schlegel PG et al., A synthetic random basic copolymer with promiscuous binding to class II major histocompatibility complex molecules inhibits T-cell proliferative responses to major and minor histocompatibility antigens in vitro and confers the capacity to prevent murine graft-versus-host disease in vivo. *Proc Natl Acad Sci U S A* May 14, 1996;93(10):5061-6.

Teitelbaum D et al., Immunomodulation of experimental autoimmune encephalomyelitis by oral administration of copolymer 1. *Proc Natl Acad Sci U S A* Mar. 30, 1999;96(7):3842-7.

Teitelbaum D et al., Specific inhibition of the T-cell response to myelin basic protein by the synthetic copolymer Cop 1. *Proc Natl Acad Sci U S A* Dec. 1988;85(24):9724-8.

Teitelbaum D et al., Synthetic copolymer 1 inhibits human T-cell lines specific for myelin basic protein. *Proc Natl Acad Sci U S A* Jan. 1, 1992;89(1):137-41.

Teitelbaum D et al., Unprimed spleen cell populations recognize macrophage-bound antigen with opposite net electric charge. *Proc Natl Acad Sci U S A* Apr. 1977;74(4):1693-6.

Tzianabos AO et al., Bacterial structure and functional relation to abscess formation. *Infect Agents Dis* 1994 3:256-65.

Tzianabos AO et al., Effect of surgical adhesion reduction devices on the propagation of experimental intra-abdominal infection. *Arch Surg* Nov. 1999;134(11):1254-9.

Tzianabos AO et al., IL-2 mediates protection against abscess formation in an experimental model of sepsis. *J Immunol* Jul. 15, 1999;163(2):893-7.

Tzianabos AO et al., Polysaccharide-mediated protection against abscess formation in experimental intra-abdominal sepsis. *J Clin Invest* Dec. 1995;96(6):2727-31.

Tzianabos AO et al., Protection against experimental intraabdominal sepsis by two polysaccharide immunomodulators. *J Infect Dis* Jul. 1998;178(1):200-6.

Tzianabos AO et al., Structural characteristics of polysaccharides that induce protection against intra-abdominal abscess formation. *Infect Immun* Nov. 1994;62(11):4881-6.

Tzianabos AO et al., Structural features of polysaccharides that induce intra-abdominal abscesses. *Science* Oct. 15, 1993;262(5132):416-9.

Tzianabos AO et al., Structure and function of *Bacteroides fragilis* capsular polysaccharides: relationship to induction and prevention of abscesses. *Clin Infect Dis* Jun. 1995;20 Suppl 2:S132-40.

Tzianabos AO et al., Structure-function relationships for polysaccharide-induced intra-abdominal abscesses. *Infect Immun* Aug. 1994;62(8):3590-3.

Tzianabos AO et al., T cells activated by zwitterionic molecules prevent abscesses induced by pathogenic bacteria. *J Biol Chem* Mar. 10, 2000;275(10):6733-40.

Tzianabos AO et al., The capsular polysaccharide of *Bacteroides fragilis* comprises two ionically linked polysaccharides. *J Biol Chem* Sep. 5, 1992;267(25):18230-5.

Wujek JR et al., A carbohydrate polymer that effectively prevents epidural fibrosis at laminectomy sites in the rat. *Exp Neurol* Nov. 1991;114(2):237-45.

Yokoyama M et al., Adhesion behavior of rat lymphocytes to poly(ether)-poly(amino acid) block and graft copolymers. *J Biomed Mater Res* Sep. 1986;20(7):867-78.

\* cited by examiner

PSA  Saline
β-Actin bp 748   
IL-2 bp 390   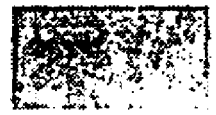
IL-4 bp 332   
IL-10 bp 358   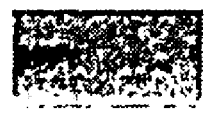
IFN-g bp 203   
Figure 7

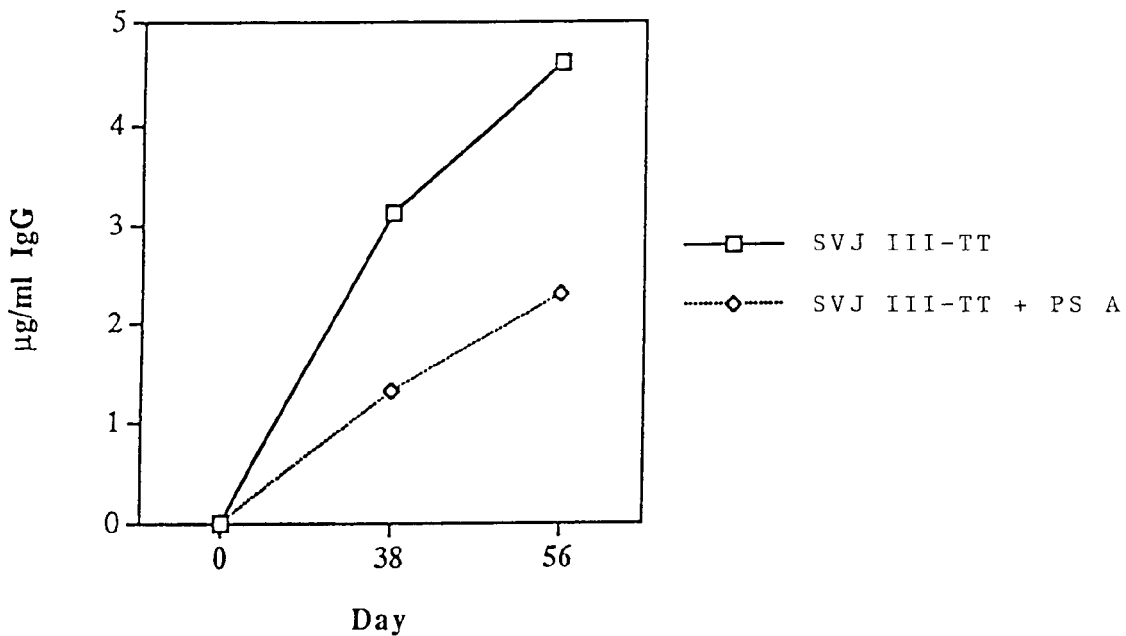
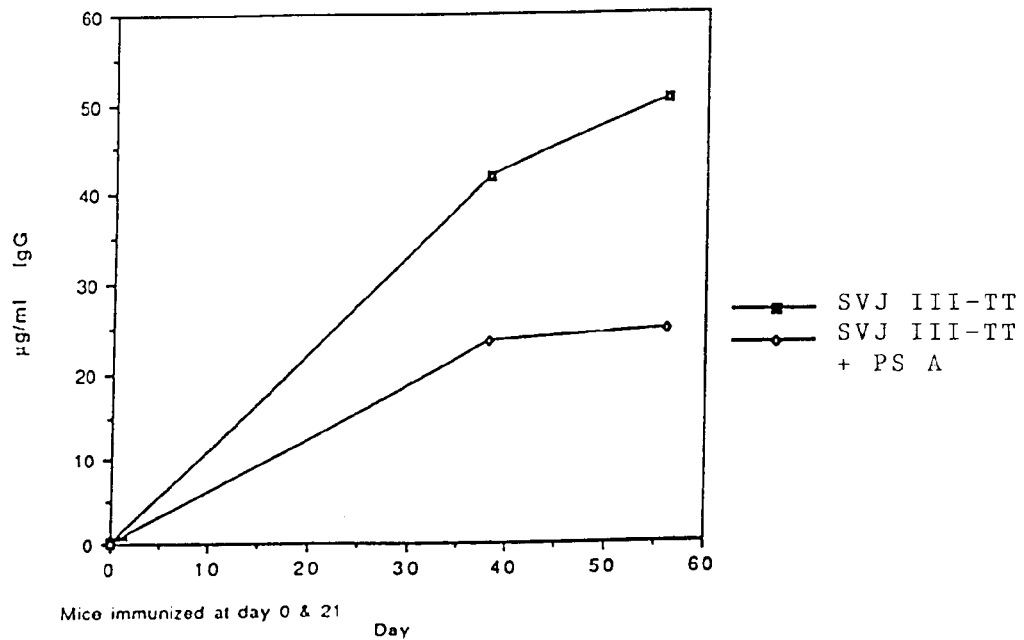
Figure 8

T cell transfer of Adhesion Reduction by *S. pneumoniae* type 1 CP

Figure 10

SEQUENCE LISTING

```
<160> NUMBER OF SEQ ID NOS: 10

<210> SEQ ID NO 1
<211> LENGTH: 21
<212> TYPE: DNA
<213> ORGANISM: Rattus norvegicus

<400> SEQUENCE: 1
ccaaccgtga aaagatgacc c                                              21

<210> SEQ ID NO 2
<211> LENGTH: 22
<212> TYPE: DNA
<213> ORGANISM: Rattus norvegicus

<400> SEQUENCE: 2
tcgtactcct gcttgctgat cc                                             22

<210> SEQ ID NO 3
<211> LENGTH: 21
<212> TYPE: DNA
<213> ORGANISM: Rattus norvegicus

<400> SEQUENCE: 3
acgcttgtcc tccttgtcaa c                                              21

<210> SEQ ID NO 4
<211> LENGTH: 22
<212> TYPE: DNA
<213> ORGANISM: Rattus norvegicus

<400> SEQUENCE: 4
ccatctcctc agaaattcca cc                                             22

<210> SEQ ID NO 5
<211> LENGTH: 22
<212> TYPE: DNA
<213> ORGANISM: Rattus norvegicus

<400> SEQUENCE: 5
gctgtcaccc tgttctgctt tc                                             22

<210> SEQ ID NO 6
<211> LENGTH: 21
<212> TYPE: DNA
<213> ORGANISM: Rattus norvegicus

<400> SEQUENCE: 6
tcattaacgg tgcagcttct c                                              21

<210> SEQ ID NO 7
<211> LENGTH: 21
<212> TYPE: DNA
<213> ORGANISM: Rattus norvegicus

<400> SEQUENCE: 7
acaataactg cacccacttc c                                              21

<210> SEQ ID NO 8
<211> LENGTH: 21
<212> TYPE: DNA
<213> ORGANISM: Rattus norvegicus
```

```
<400> SEQUENCE: 8
aaatcattct tcacctgctc c                                             21

<210> SEQ ID NO 9
<211> LENGTH: 23
<212> TYPE: DNA
<213> ORGANISM: Rattus norvegicus

<400> SEQUENCE: 9
ccatcagcaa caacataagt gtc                                           23

<210> SEQ ID NO 10
<211> LENGTH: 21
<212> TYPE: DNA
<213> ORGANISM: Rattus norvegicus

<400> SEQUENCE: 10 actcctttc cgcttcctta g                                              21
```

IMMUNOMODULATING POLYMERS

RELATED APPLICATIONS

This application claims priority to U.S. Provisional Patent Application No. 60/127,584, filed Apr. 2, 1999, and to U.S. Provisional Patent Application No. 60/162,457, filed Oct. 29, 1999, the entire contents of which are hereby incorporated by reference.

GOVERNMENT SUPPORT

The present invention was supported in part by a grant from the United States National Institutes of Health AI 34073 and AI 39576. The U.S. Government may retain certain rights in the invention.

FIELD OF THE INVENTION

The present invention relates to immunomodulators and methods for modulating an immune response. The invention also relates to methods for activating T cells, inducing IL-2, protecting a subject against abscess formation associated with bacterial infection or contamination, and reducing postoperative surgical adhesion formation in a subject.

BACKGROUND OF THE INVENTION

A commonly occurring complication associated with leakage of colonic bacteria into the peritoneum is intraabdominal sepsis and abscess formation. An abscess is an encapsulated collection of bacteria, lymphocytes, macrophages, polymorphonuclear leukocytes and fibrin that forms in response to bacterial insult or contamination within a tissue or body cavity, such as occurs during a surgical procedure, trauma or diseases such as appendicitis or cancer. Invasion of the exposed body area by the bacteria may occur in a localized area within the peritoneal cavity, retroperitoneal space, pelvis or other spaces or organs in the body. The infected tissue area remains relatively immune to antibiotics which are unable to penetrate the tissue structures and effectively clear walled-off bacteria. If the abscess is left untreated, it may cause fever, prolonged hospitalization, and in some cases mortality. If the abscess ruptures, it will release its bacterial contents into the peritoneal cavity, which can in turn lead to recurring sepsis in these patients. Currently when abdominal surgeries are performed, antibiotics are administered prophylactically as well as postoperatively. However, once an abscess has formed, the major course of action is further surgical intervention to drain the offending abscess, a time-consuming and costly procedure.

It has been impractical to immunize patients against abscess formation such as in the case of intraabdominal surgery because there simply are too many strains of bacteria capable of causing abscess formation, and protection against one would not confer protection against another. It furthermore is unsettled whether vaccination and consequent induction of an immune response would confer adequate protection against abscess formation by any particular bacterium. There also exist problems and dangers associated with administering live or attenuated strains of bacteria to humans, further discouraging efforts to produce vaccines containing a large number of different bacteria.

Capsular polysaccharides of bacteria can be found covering the surface of some bacteria pathogenic to humans. Polysaccharides have been characterized as T cell-independent antigens that elicit only humoral antibody responses. Although many polysaccharides have been shown to be immunogenic, some are only weakly immunogenic at best.

Bacteroides fragilis is a predominant obligate anaerobe isolated from intraabdominal abscesses. The capsular polysaccharide complex (CPC) has been identified as the region of B. fragilis which causes abscess formation. This carbohydrate complex covers the surface of B. fragilis. The isolated complex alone can interact with the host immune system, in the presence of adjuvant (sterile cecal contents and barium sulphate), to elicit a patho-biologic response that results in fully formed intraperitoneal abscesses in individuals injected intraperitoneally with the complex. Studies were performed in rodent models in which B. fragilis or its CPC were injected intra peritoneally. Both intact B. fragilis and CPC alone provoked abscess formation associated with intraabdominal sepsis.

It was investigated whether the CPC of B. fragilis could be used to immunize subjects against subsequent infection and abscess formation by B. fragilis. It was by no means predictable that this would be possible based upon the property of CPC alone to provoke abscess formation since "immunity" and abscess formation are not known to result from remotely related immunological responses. When CPC was administered subcutaneously it was found to confer immunological protection against intraperitoneal CPC-mediated abscess induction in a rat model. Protection against abscess formation by this polysaccharide complex was determined to be mediated by a T cell-dependent host response.

Although subcutaneous administration of either B. fragilis or CPC is sufficient to protect animals against abscess formation subsequent to challenge with B. fragilis or CPC, neither conferred immunity against other bacterial strains, as was expected. They therefore have no use as a "vaccine" for abscess formation caused by the multitude of organisms normally found in the colon.

The CPC consists of two distinct high molecular weight polysaccharides, termed A and B. Each polysaccharide is composed of distinct oligosaccharide repeating units possessing uncommon constituent sugars with free amino, carboxyl and phosphonate groups. Polysaccharide A (PS A) has a tetrasaccharide repeating unit with a balanced positively charged amino group and negatively charged carboxyl group. Polysaccharide B has a hexasaccharide repeating unit, including an unusual 2-amino ethylphosphonate substituent containing a free amino group and negatively charged phosphate group. The galacturonic acid residue contains an additional negatively charged carboxyl group. Ionic interaction between the two saccharide chains tightly links polysaccharides A and B into the high molecular weight CPC complex. The complex capsular motif is a conserved trait for all strains of B. fragilis that have thus far been examined.

Recently it was discovered that polysaccharides having a particular structural motif can protect animals against challenge with abscess-inducing bacteria. U.S. Pat. Nos. 5,700,787 and 5,679,654. Preferably the polysaccharides are polymers of repeating units of a charge motif characteristic of polysaccharide A of B. fragilis, the motif being a positively charged free amino moiety and a negatively charged moiety selected from the group consisting of carboxyl, phosphate, phosphonate, sulfate and sulfonate. Such polymers are capable of inducing "cross-protection." That is, a single polymer can produce protection against abscess formation by a variety of bacteria. Thus the polymers are useful for inducing protection against abscess formation associated with surgery, trauma or diseases that predispose the host to abscess formation. A pharmaceutical preparation of the polymer is administered to a subject in conjunction with intraabdominal surgery or upon presentation of a predisposing condition.

It was also reported in the prior art that while several types of cytokines, such as interleukin-10 (IL-10), are useful as general immunomodulators for blocking abscess formation, other cytokines, such as interleukin-2 (IL-2), tumor necrosis factor, and interferon, may participate in abscess formation, since antibodies specific for such substances can help block abscess formation. U.S. Pat. No. 5,700,787.

Postoperative surgical adhesions are a major complication of abdominal, pelvic, gynecologic, cardiothoracic, orthopedic and neurosurgical surgeries. Surgical adhesions within the abdomen are associated with a high morbidity rate and can be fatal. They can result in bowel obstruction and organ failure. There are approximately 1.5 million abdominal surgeries performed every year in the United States alone. Of these surgeries 25 to 35 percent of cases result in the development of surgical adhesions. Repair of adhesions that cause bowel obstruction and organ failure require reoperation for their removal.

Traditionally these adhesions have been thought to be caused by a combination of factors including manipulative trauma and drying of the tissues during the surgery itself. A number of techniques attempting to ameliorate these problems have been previously described. Current clinical methods directed toward reducing the formation of postoperative surgical adhesions generally rely on placement of a film or gel directly into the operative site with the intention of creating a physical barrier between surfaces likely to become involved in adhesion formation. These methods remain cumbersome for the surgeon. Highly concentrated solutions of a number of polymers have been used to coat the surgical area before and during surgery so as to minimize the drying and act as cushion to prevent some of the manipulative trauma. Examples of the techniques are described in U.S. Pat. No. 4,819,617 to Goldberg et al. and U.S. Pat. No. 4,886,787 to De Belder et al. Among the materials used are polyvinylpyrrolidone (PVP), dextrans, carboxymethylcelluloses, and a number of other polymers such as protein or polypeptide solutions.

One polymer which has been used to reduce postoperative surgical adhesion formation is hyaluronic acid (HA). A series of patents by Goldberg et al., particularly U.S. Pat. No. 5,140,016, shows the use of pretreatment of surgical sites with hyaluronic acid solutions as a means of preventing surgical adhesions. Goldberg disclosed that dilute solutions of high molecular weight HA (>500 kDa) are effective at concentrations of 0.01 to 0.6% (weight/volume) when used for surgical adhesion prevention. A 0.01% solution of about 1500 kDa molecular weight HA effectively prevents all severe intra-abdominal adhesions in a rat adhesion model that normally produces more than 70% adhesions.

Like abscess formation, postoperative surgical adhesion formation involves fibrin deposition within a site of inflammation. While the exact mechanism underlying adhesion formation remains unknown, much attention has been directed to the apparent role of transforming growth factor beta (TGF-β), particularly TGF-β1. TGF-β is a key factor in the regulation of the inflammatory response and the production of extracellular matrix by fibroblasts. These two processes are linked in the formation of fibrous adhesions following abdominal surgery. TGF-β also increases the synthesis of integrin receptors, thereby enhancing interaction between cell and extracellular matrix. Using a model of abdominal adhesions in rats, Lucas et al. demonstrated that rats injected with anti-TGF-β1 had significantly lower adhesion scores than rats receiving control IgG, anti-TGF-β2 or panspecific anti-TGF-β. Lucas, P A et al. *J Surg Res* 65:135 (1996).

U.S. Pat. No. 5,679,658 to Elson discloses a method of preventing surgical adhesions in which a surgical site is coated with an effective amount of a covalently crosslinked N,O-carboxymethylchitosan (NOCC) gel and ravaged with a solution of uncrosslinked NOCC after surgical manipulation. NOCC is a polymer in which carboxymethyl substituants are present on some of both the amino and primary hydroxyl sites of the glucosamine units of the chitosan structure. U.S. Pat. No. 4,619,995 to Hayes. NOCC can be crosslinked into a stable gel using conventional methods known in the art. Krause et al. investigated the possibility that effects of NOCC on adhesion formation reflect the modulation of TGF-β activity. Krause, T J et al. *J Invest Surg* 11: 105 (1998). Using a cecal abrasion model in the rat, Krause et al. reported that NOCC suppresses the levels of an inhibitor of cell proliferation released into serum and peritoneal cavity. However, this activity is distinct from known forms of TGF-β as determined using both TGF-β neutralizing anti-sera and a TGF-β resistant cell proliferation assay. Krause et al. concluded that at least one potential effect of NOCC involves a mechanism distinct from TGF-β inhibition.

In view of the foregoing, a need still exists to develop compositions and methods for treating and/or preventing abscess formation, surgical adhesion formation, and other immune-related disorders.

SUMMARY OF THE INVENTION

The present invention relates to methods and products for inducing IL-2 secretion, activating T cells to produce a Th1 cytokine profile, suppressing IgG antibody response to specific antigen, promoting allograft survival, protecting against abscess formation associated with surgery, trauma or diseases that predispose the host to abscess formation, and reducing postoperative surgical adhesion formation. The methods of the invention are accomplished using an immunomodulator which is a polymer, or in some aspects of the invention a polypeptide, having at least two repeating charge motifs. The repeating charge motif is composed of a positively charged free amino moiety and a negative charge. The at least two repeating charge motifs are separated from one another by a minimum distance. The minimum length of the polymer is thus the length of a polymer having one repeating charge motif at one end and the other at the opposite end, separated by a number of units. This minimum length of the polymer is the equivalent of 10 amino acid residues.

The invention in one aspect encompasses pharmaceutical compositions. The pharmaceutical composition in this aspect is a polypeptide of less than 50 kilodaltons (kDa) having at least two repeating charge motifs, wherein the repeating charge motif is composed of a positively charged free amino moiety and a negative charge, wherein the positively charged free amino moieties of the at least two repeating charge motifs are separated by a distance of at least 8 amino acid residues and a pharmaceutically acceptable carrier. In other embodiments the at least two repeating charge motifs are separated by a distance of at least 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 amino acid residues.

In another aspect the invention is a pharmaceutical composition of a polymer of less than 50 kilodaltons having at least two repeating charge motifs, wherein the repeating charge motif is composed of a positively charged free amino moiety and a negative charge, wherein the positively charged free amino moieties of the at least two repeating charge motifs are separated by an intervening sequence, the length of which is at least that corresponding to the minimum distance separating the ends of an 8-amino acid long oligomer in aqueous solution, and wherein the intervening sequence is neutral, and a pharmaceutically acceptable carrier. In one embodiment the polymer is a mixed polymer. In another embodiment the mixed polymer is a peptide-nucleic acid. In other embodiments the at least two repeating charge motifs are separated by a distance of at least 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 amino acid residues.

The polymer or polypeptide may be composed of many different combinations of units as long as it has a repeating charge motif. In one embodiment the polymer or polypeptide has non-repeating units. In another embodiment the polymer or polypeptide has repeating units. When the polymer has repeating units the repeating units may be identical repeating units or non-identical repeating units.

The polymer or polypeptide may have more than two repeating charge motifs. In one embodiment the polymer or polypeptide has at least 10 repeating charge motifs. In another embodiment the polymer or polypeptide has at least 15 repeating charge motifs. In yet another embodiment the polymer or polypeptide has at least 20 repeating charge motifs.

The space between the repeating charged units may be composed entirely or partially of repeating or non-repeating charged units. Alternatively the space between the repeating charged units may be composed of an intervening sequence, composed entirely of neutral units.

The positive and negative charges of the repeating charge motifs may be on adjacent units and thus may not be separated by any neutral amino acids. In an alternative embodiment the positive and negative charges of the repeating charge motifs are separated by at least one neutral unit. In another embodiment the positive and negative charges of the repeating charge motifs are separated by at least five neutral units.

According to one embodiment of the invention positively charged free amino moieties of the at least two repeating charge motifs are separated by a distance of at least 115 Å. In another embodiment the positively charged free amino moieties of the at least two repeating charge motifs are separated by a distance of at least 155 Å. In a preferred embodiment the positively charged free amino moieties of the at least two repeating charge motifs are separated by a distance of at least 200 Å.

When the polymer is a polypeptide it may be a natural polypeptide or a synthetic polypeptide. The polymer may also be a native or a non-native polypeptide. In one embodiment the polypeptide may have at least one modified amino acid. In another embodiment the polypeptide has at least ten modified amino acids. According to yet another embodiment the polypeptide may have a positive to negative charge ratio of 1:1. When the polymer is a polypeptide in some embodiments the polymer does not consist of lysine (K), glutamic acid (E), alanine (A), and tyrosine (Y) residues in a relative molar ratio of 3–7 parts of K to 1–3 parts of E to 4–7 parts of A, to 0.5–2 parts of Y.

It has been discovered according to the invention that the immunomodulating polymers described above as well as those described below are capable of inducing immune-specific responses such as inducing IL-2 secretion, inducing IL-10 secretion, activating T cells to produce Th1 cytokines, and suppressing antigen-specific IgG antibody production. It has also been discovered that the polymers are useful for preventing abscess formation, treating IL-2-responsive or Th1-responsive disorders, treating autoimmune disease or promoting allograft survival.

In one aspect the method for inducing interleukin 2 (IL-2) secretion involves the following steps: contacting an IL-2 secreting cell with an effective amount for inducing IL-2 secretion of a polymer of less than 50 kilodaltons having at least two repeating charge motifs, wherein the repeating charge motif is composed of a positively charged free amino moiety and a negative charge, wherein the positively charged free amino moieties of the at least two repeating charge motifs are separated by a distance of at least 32 Å and wherein the polymer has non-repeating units.

In another aspect the method for inducing interleukin 2 (IL-2) secretion involves the following steps: contacting an IL-2 secreting cell with an effective amount for inducing IL-2 secretion of a polypeptide of less than 50 kilodaltons having at least two repeating charge motifs, wherein the repeating charge motif is composed of a positively charged free amino moiety and a negative charge, wherein the positively charged free amino moieties of the at least two repeating charge motifs are separated by a distance of at least 8 amino acid residues. In one embodiment the polypeptide is formed of repeating units and wherein the repeating charge motif is at least part of the repeating unit. In other embodiments the at least two repeating charge motifs are separated by a distance of at least 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 amino acid residues.

In another aspect the invention is a method for treating an IL-2-responsive disorder by inducing IL-2 secretion. The method includes the steps of administering to a subject having an IL-2-responsive disorder an effective amount for inducing IL-2 secretion a polymer of less than 50 kilodaltons having at least two repeating charge motifs, wherein the repeating charge motif is composed of a positively charged free amino moiety and a negative charge, wherein the positively charged free amino moieties of the at least two repeating charge motifs are separated by a distance of at least 32 Å and wherein the subject is not preparing to undergo surgery.

In one embodiment the polymer is any polymer of the novel pharmaceutical preparations described above. In another embodiment the polymer is a polypeptide. According to another embodiment the positively charged free amino moiety results from a naturally occurring positively charged amino acid. Preferably the positively charged amino acid is selected from the group consisting of lysine (K), arginine (R), asparagine (N) and histidine (H). Preferably the positively charged amino acid is lysine. In another embodiment the negative charge results from a naturally occurring negatively charged amino acid. Preferably the negatively charged amino acid is selected from the group consisting of aspartic acid (D) and glutamic acid (E). In a preferred embodiment the negatively charged amino acid is aspartic acid.

The polymer or polypeptide may be composed of many different combinations of units as long as it has a repeating charge motif. In one embodiment the polymer or polypeptide has non-repeating units. In another embodiment the polymer or polypeptide has repeating units. When the polymer has repeating units the repeating units may be identical repeating units or non-identical repeating units.

The polymer or polypeptide may have more than two repeating charge motifs. In one embodiment the polymer or polypeptide has at least 10 repeating charge motifs. In another embodiment the polymer or polypeptide has at least 15 repeating charge motifs. In yet another embodiment the polymer or polypeptide has at least 20 repeating charge motifs.

The space between the repeating charged units may be composed entirely or partially of repeating or non-repeating charged units. Alternatively the space between the repeating charged units may be composed of an intervening sequence, composed entirely of neutral units.

The positive and negative charges of the repeating charge motifs may be on adjacent units and thus may not be separated by any neutral amino acids. In an alternative embodiment the positive and negative charges of the repeating charge motifs are separated by at least one neutral unit. In another embodiment the positive and negative charges of the repeating charge motifs are separated by at least five neutral units.

According to one embodiment of the invention positively charged free amino moieties of the at least two repeating charge motifs are separated by a distance of at least 115 Å. In another embodiment the positively charged free amino moieties of the at least two repeating charge motifs are separated by a distance of at least 155 Å. In a preferred embodiment the positively charged free amino moieties of the at least two repeating charge motifs are separated by a distance of at least 200 Å.

The polymer may be any type of polymer, synthetic or natural, native or non-native, etc. The polymer may have natural units or chemically modified units such as a polypeptide having at least one modified, i.e., chemically modified, amino acid. In one embodiment the polypeptide has at least ten modified amino acids.

In another embodiment the polymer has a positive to negative charge ratio of 1:1.

According to yet another embodiment the IL-2-responsive disorder is a disorder selected from the group consisting of AIDS, cancer, autoimmune disease.

Surprisingly, it was discovered according to the invention that IL-2 is capable of inducing protection against abscess formation in a subject at risk of developing an abscess. This can be accomplished by administering exogenous IL-2 or IL-2 inducing agents to the subject. Prior to the invention it was believed in the art that IL-2 may contribute to abscess formation. It was surprisingly discovered that IL-2 actually helps to prevent abscess induction.

Thus in one aspect the invention is a method for inducing protection against abscess formation associated with infection. The method includes the step of administering to a subject in need of such protection a pharmaceutical preparation containing an effective amount for inducing protection against abscess formation of a compound selected from the group consisting of IL-2 and an IL-2 inducing compound. In one embodiment the IL-2 inducing compound is selected from the group consisting of an activated Th1 cell, staphylococcal enterotoxin A (SEA), an anti-CD3 antibody, an oxidative chemical, and tucaresol (4[2-formyl-3-hydroxyphenoxymethyl] benzoic acid).

It has also been discovered according to the invention that T cells activated by the polymers described above are capable of inducing protection against abscess formation in a subject at risk of developing an abscess. Thus in one aspect the invention encompasses a method for inducing protection against abscess formation associated with infection. The method includes the step of administering to a subject in need of such protection a pharmaceutical preparation containing an effective amount for inducing protection against abscess formation of a polymer of less than 50 kilodaltons having at least two repeating charge motifs, wherein the repeating charge motif is composed of a positively charged free amino moiety and a negative charge, wherein the positively charged free amino moieties of the at least two repeating charge motifs are separated by a distance of at least 32 Å and wherein the polymer has non-repeating units.

In another aspect the invention is a method for inducing protection against abscess formation associated with infection that includes the step of administering to a subject in need of such protection a pharmaceutical preparation containing an effective amount for inducing protection against abscess formation of a polypeptide of less than 50 kilodaltons having at least two repeating charge motifs, wherein the repeating charge motif is composed of a positively charged free amino moiety and a negative charge, wherein the positively charged free amino moieties of the at least two repeating charge motifs are separated by a distance of at least 8 amino acid residues. Preferably the polypeptide is formed of repeating units and wherein the repeating charge motif is at least part of the repeating unit. In other embodiments the at least two repeating charge motifs are separated by a distance of at least 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 amino acid residues.

The pharmaceutical preparation useful for inducing protection against abscess formation in one embodiment induces IL-2. According to another embodiment of this aspect of the invention, the pharmaceutical preparation useful for inducing protection against abscess formation induces IL-10.

The subject in need of protection is a subject at risk of developing an abscess. In one embodiment the pharmaceutical preparation is administered to the subject before the subject has been exposed to abscess forming conditions. In another embodiment the pharmaceutical preparation is administered to the subject after the subject has been exposed to abscess forming conditions. The pharmaceutical preparation in yet another embodiment is administered to a subject in need of surgery. In another embodiment the pharmaceutical preparation is administered to a subject who has undergone surgery.

The pharmaceutical preparation may be administered alone or in conjunction with other compounds. In one embodiment the pharmaceutical preparation is given in conjunction with one or more anti-bacterial agents selected from the group consisting of penicillin G, penicillin V, ampicillin, amoxicillin, bacampicillin, cyclacillin, epicillin, hetacillin, pivampicillin, methicillin, nafcillin, oxacillin, cloxacillin, dicloxacillin, flucloxacillin, carbenicillin, ticarcillin, avlocillin, mezlocillin, piperacillin, amdinocillin, cephalexin, cephradine, cefadoxil, cefaclor, cefazolin, cefuroxime axetil, cefamandole, cefonicid, cefoxitin, cefotaxime, ceftizoxime, cefinenoxine, ceftriaxone, moxalactam, cefotetan, cefoperazone, ceftazidme, imipenem, clavulanate, timentin, sulbactam, neomycin, erythromycin, metronidazole, chloramphenicol, clindamycin, lincomycin, vancomycin, trimethoprim-sulfamethoxazole, aminoglycosides, quinolones, tetracyclines and rifampin.

In some embodiments the polymer is a polysaccharide and in other embodiments it is a non-polysaccharide. In yet other embodiments the polymer is a peptide and in others it is a non-peptide.

It has also been discovered according to the invention that the polymers described above are capable of inducing protection against postoperative surgical adhesion formation in a subject at risk of developing a postoperative surgical adhesion. Thus in one aspect the invention encompasses a method for reducing postoperative surgical adhesion formation. The method includes the step of administering to a subject in need of such protection a pharmaceutical preparation containing an effective amount for inducing protection against postoperative surgical adhesion formation of a zwitterionic polymer having at least two repeating charge motifs, wherein the repeating charge motif is composed of a positively charged free amino moiety and a negative charge, wherein the positively charged free amino moieties of the at least two repeating charge motifs are separated by a distance of at least 32 Å.

The pharmaceutical preparation useful for reducing postoperative surgical adhesion formation at a surgical site in one embodiment induces IL-2. According to another embodiment of this aspect of the invention, the pharmaceutical preparation useful for reducing postoperative surgical adhesion formation at a surgical site induces IL-10.

In one aspect of the invention is a method for reducing postoperative surgical adhesion formation at a surgical site that includes the step of administering to a subject in need of such protection, at a site other than at the surgical site, a pharmaceutical preparation containing an effective amount for reducing postoperative surgical adhesion formation of a zwitterionic polymer having at least two repeating charge motifs, wherein the repeating charge motif is composed of a positively charged free amino moiety and a negative charge, wherein the positively charged free amino moieties of the at least two repeating charge motifs are separated by a distance of at least 32 Å.

In another aspect of the invention is a method for reducing postoperative surgical adhesion formation occurring at a surgical site that includes the step of locally administering to the surgical site of a subject in need of such protection a pharmaceutical preparation containing an effective amount for producing protection against postoperative surgical adhesion formation of a zwitterionic non-polysaccharide polymer having at least two repeating charge motifs, wherein the repeating charge motif is composed of a positively charged free amino moiety and a negative charge, wherein the positively charged free amino moieties of the at least two repeating charge motifs are separated by a distance of at least 32 Å.

In another aspect the invention is a method for reducing postoperative surgical adhesion formation that includes the step of administering to a subject in need of such protection a pharmaceutical preparation containing an effective amount for reducing postoperative surgical adhesion formation of a zwitterionic polypeptide of less than 50 kilodaltons having at least two repeating charge motifs, wherein the repeating charge motif is composed of a positively charged free amino moiety and a negative charge, wherein the positively charged free amino moieties of the at least two repeating charge motifs are separated by a distance of at least 8 amino acid residues. Preferably the polypeptide is formed of repeating units and wherein the repeating charge motif is at least part of the repeating unit. In other embodiments the at least two repeating charge motifs are separated by a distance of at least 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 amino acid residues.

In yet another aspect the invention is a method for reducing postoperative surgical adhesion formation that includes the step of locally administering to the surgical site of a subject in need of such protection a pharmaceutical preparation containing an effective amount for producing protection against postoperative surgical adhesion formation of a zwitterionic polysaccharide polymer having at least two repeating charge motifs, wherein the repeating charge motif is composed of a positively charged free amino moiety and a negative charge, wherein the positively charged free amino moieties of the at least two repeating charge motifs are separated by a distance of at least 32 Å; the polysaccharide polymer has a molecular weight less than about 500 kilodaltons; and the polysaccharide polymer is not N,O-carboxymethylchitosan or a derivative thereof.

In certain embodiments the polymers of the invention useful for reducing postoperative surgical adhesion formation can be at least partly crosslinked and can form a gel. In other embodiments the polymers of the invention useful for reducing postoperative surgical adhesion formation can be uncrosslinked and can be used in solution.

In certain embodiments the polymers of the invention useful for reducing postoperative surgical adhesion formation can range in molecular weight from about 1.5 kilodaltons to about 50 kilodaltons. In other embodiments the polymers of the invention useful for reducing postoperative surgical adhesion formation can range in molecular weight from greater than about 50 kilodaltons to less than about 500 kilodaltons. In still other embodiments the polymers of the invention useful for reducing postoperative surgical adhesion formation can range in molecular weight from greater than or equal to about 500 kilodaltons to about 5000 kilodaltons.

In certain embodiments the amount of polymer of the invention effective for reducing postoperative surgical adhesion formation can range between about 1 to 10 mg/kg of subject body weight.

The subject in need of reducing postoperative surgical adhesion formation is a subject at risk of developing an postoperative surgical adhesion. In one embodiment the pharmaceutical preparation is administered to the subject beginning before the subject has been exposed to postoperative surgical adhesion forming conditions. In another embodiment the pharmaceutical preparation is administered to the subject after the subject has been exposed to postoperative surgical adhesion forming conditions. The pharmaceutical preparation in yet another embodiment is administered to a subject in need of surgery. In another embodiment the pharmaceutical preparation is administered to a subject who has undergone surgery.

According to another aspect, the invention is a method of activating T cells. The method includes the step of contacting a T cell in the presence of an antigen-presenting cell with an effective amount for inducing IL-2 secretion of a polymer of less than 50 kilodaltons having at least two repeating charge motifs, wherein the repeating charge motif is composed of a positively charged free amino moiety and a negative charge, wherein the positively charged free amino moieties of the at least two repeating charge motifs are separated by a distance of at least 32 Å and wherein the polypeptide has non-repeating units.

In another aspect the invention is a method of activating T cells, the method including the step of contacting a T cell in the presence of an antigen presenting cell with an effective amount for inducing IL-2 secretion of a polypeptide of less than 50 kilodaltons having at least two repeating charge motifs, wherein the repeating charge motif is composed of a positively charged free amino moiety and a negative charge, wherein the positively charged free amino moieties of the at least two repeating charge motifs are separated by a distance of at least 8 amino acid residues. Preferably the polypeptide is formed of repeating units and wherein the repeating charge motif is at least part of the repeating unit. In other embodiments the at least two repeating charge motifs are separated by a distance of at least 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 amino acid residues.

According to yet another aspect, the invention is a method for treating a Th1-cell-responsive disorder by activating a T cell to produce Th1-cell-specific cytokines. The method includes the step of administering to a subject having a Th1-cell-responsive disorder an effective amount for inducing IL-2 secretion by the T cell a polymer of less than 50 kilodaltons having at least two repeating charge motifs, wherein the repeating charge motif is composed of a positively charged free amino moiety and a negative charge, wherein the positively charged free amino moieties of the at least two repeating charge motifs are separated by a distance of at least 32 Å and wherein the subject is not preparing to undergo surgery.

In one embodiment the Th1-cell-responsive disorder is selected from the group consisting of insulin-dependent diabetes mellitus, experimental allergic encephalomyelitis, inflammatory bowel disease, and allograft rejection.

The invention according to another aspect is a method for treating a subject having a disorder characterized by an inappropriate IgG antibody response to specific antigen. The method includes the step of administering to a subject having a disorder characterized by an inappropriate IgG antibody a pharmaceutical preparation containing an effective amount for suppressing IgG antibody response to specific antigen of a polymer of less than 50 kilodaltons having at least two repeating charge motifs, wherein the repeating charge motif is composed of a positively charged free amino moiety and a negative charge, wherein the positively charged free amino moieties of the at least two repeating charge motifs are separated by a distance of at least 32 Å, wherein when the polymer is a polypeptide the polymer does not consist of lysine (K), glutamic acid (E), alanine (A), and tyrosine (Y) residues in a relative molar ratio of 3–7 parts of K to 1–3 parts of E to 4–7 parts of A, to 0.5–2 parts of Y, and wherein the subject is not preparing to undergo surgery.

Preferably, the pharmaceutical preparation is administered to the subject once a day. In one embodiment the pharmaceutical preparation has a positive to negative charge ratio of 1:1.

The invention in another aspect is a method for promoting allograft survival. The method includes the step of administering to a subject in need of such treatment a pharmaceutical preparation containing an effective amount for promoting allograft survival of a polypeptide of less than 50 kilodaltons having at least two repeating charge motifs, wherein the repeating charge motif is composed of a positively charged free amino moiety and a negative charge, wherein the positively charged free amino moieties of the at least two repeating charge motifs are separated by a distance of at least 8 amino acid residues, and wherein when the polymer is a polypeptide the polymer does not consist of lysine (K), glutamic acid (E), alanine (A), and tyrosine (Y) residues in a relative molar ratio of 3–7 parts of K to 1–3 parts of E to 4–7 parts of A, to 0.5–2 parts of Y, and wherein the subject is not preparing to undergo surgery. In one embodiment the pharmaceutical preparation is administered to the subject once a day following allograft transplant. In other embodiments the at least two repeating charge motifs are separated by a distance of at least 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 amino acid residues.

Each of the limitations of the invention can encompass various embodiments of the invention. It is, therefore, anticipated that each of the limitations of the invention involving any one element or combinations of elements can be included in each aspect of the invention.

BRIEF DESCRIPTION OF THE DRAWINGS

FIG. 7. Comparative expression of IL-2, IFN-γ, IL-4, and IL-10 mRNA from T cells harvested from saline- and PS A-treated animals. Total RNA was subjected to RT-PCR. β-actin was used as the positive control. T cells from saline-treated animals did not express transcripts for these cytokines, while T cells from PS A-treated animals expressed transcripts for IL-2, IFN-γ, and IL-10.

FIG. 8. Antibody suppression induced by PS A treatment. SVJ mice were treated with 50 µg PS A or saline and immunized with conjugate vaccine containing type III group B *streptococcus* polysaccharide (GBS type III capsule) and tetanus toxoid (TT). Antigen-specific IgG responses were assayed by ELISA 38 and 56 days after primary antigen exposure. Top: IgG response to GBS type III capsule; bottom: IgG response to TT.

FIG. 10. T cell transfer of adhesion reduction. T cells from donors pretreated with saline or *Streptococcus pneumoniae* type 1 CP were transferred into rats 24 hours prior to adhesion induction. Adhesions were scored six days later.

BRIEF DESCRIPTION OF THE SEQUENCES

Figure 1:
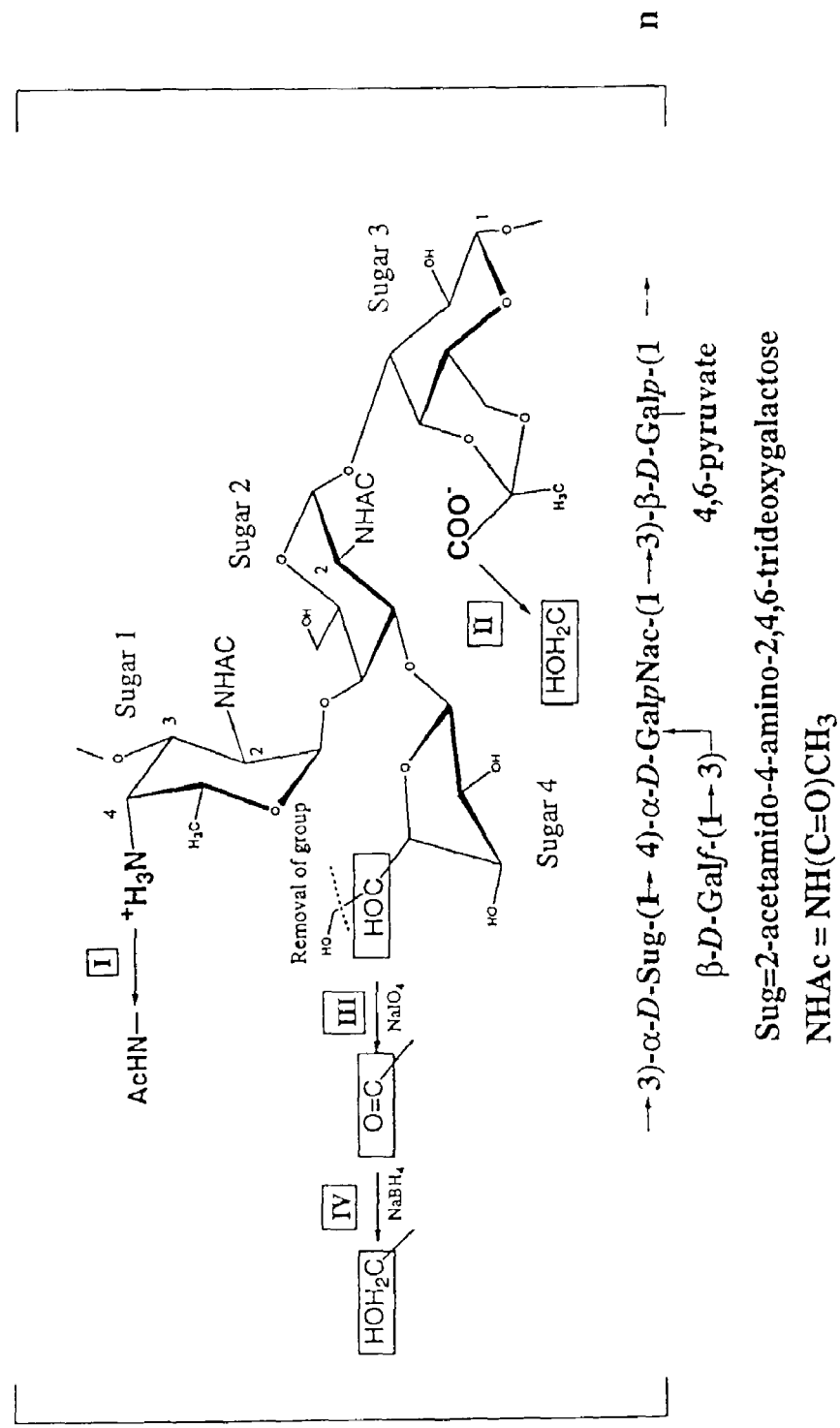
FIG. 1. Fine structure of B. fragilis PS A. This polysaccharide is composed of approximately 200 tetrasaccharide repeating units and possesses free amino, N-acetyl, and carboxyl groups. Treatment with acetic anhydride converts all free amino groups to N-acetyl groups as in Modification I. The negatively charged carboxyl groups associated with the pyruvate substituent can be reduced by carbodiimide reduction (Modification II). Periodate oxidation (0.01M $NaIO_4$ for 90 minutes at room temperature) specifically cleaves C6 from the galactofuranose side-chain (Sugar 4, Modification III), leaving an aldehyde group (CHO) at C5. Subsequent modification of the oxidized PS A by reduction with sodium borohydride ($NaBH_4$) reduces the aldehyde at C5 to a hydroxymethyl group (as in Modification IV) and thus converts the galactofuranose side-chain to arabinofuranose.

SEQ ID NO:1 is the nucleic acid sequence of the sense primer for amplification of β-actin cDNA.

SEQ ID NO:2 is the nucleic acid sequence of the antisense primer for amplification of β-actin cDNA.

SEQ ID NO:3 is the nucleic acid sequence of the sense primer for amplification of IL-2 cDNA.

SEQ ID NO:4 is the nucleic acid sequence of the antisense primer for amplification of IL-2 cDNA.

SEQ ID NO:5 is the nucleic acid sequence of the sense primer for amplification of IL-4 cDNA.

SEQ ID NO:6 is the nucleic acid sequence of the antisense primer for amplification of IL-4 cDNA.

SEQ ID NO:7 is the nucleic acid sequence of the sense primer for amplification of IL-10 cDNA.

SEQ ID NO:8 is the nucleic acid sequence of the antisense primer for amplification of IL-10 cDNA.

SEQ ID NO:9 is the nucleic acid sequence of the sense primer for amplification of IFN-γ cDNA.

SEQ ID NO:10 is the nucleic acid sequence of the antisense primer for amplification of IFN-γ cDNA.

DETAILED DESCRIPTION OF THE INVENTION

It has been discovered according to the invention that immunomodulating polymers are useful for manipulating immune cells in vivo, in vitro, and ex vivo and for treating several types of immune-related disorders. The immuno-modulating polymers described herein can alter immune cell function by inducing IL-2 production, inducing IL-10 production, activating T cells, and suppressing antigen-specific IgG antibody production. The group of compounds which are the immunomodulating polymers preferably have at least two positively charged free amino groups and at least two negatively charged groups.

It was determined that there are particular structural features on polymers which mediate the ability to modulate the immune system. Previously it has been demonstrated that polysaccharides having the charge motif of *B. fragilis* capsular polysaccharide A (PS A) can abrogate abscess induction by many types of bacteria. It has now been discovered that these polysaccharides have other immune-modulating activity in addition to the ability to prevent abscess formation. It has also been discovered that other polymers, including non-polysaccharide polymers such as polypeptides and peptide-nucleic acids having a similar charge structure can also modulate immune function in a manner similar to the polysaccharides. This was surprising in part because the immunomodulating non-polysaccharide polymers of the invention maintain this function even when they are orders of magnitude smaller (i.e., 1.5–5 kDa) than the immunomodulating polysaccharides (i.e. greater than 50 kDa).

Both the positively and negatively charged groups on these polymers modulate their ability to influence the immune system and to protect animals against abscess formation. Total neutralization of either charge abrogates the immunomodulating ability of the polymers.

The invention relates to pharmaceutical compositions of immunomodulating polymers and methods of use thereof. In one aspect the invention is a pharmaceutical composition of a polymer of less than 50 kilodaltons having at least two repeating charge motifs, wherein the repeating charge motif is composed of a positively charged free amino moiety and a negative charge, wherein the positively charged free amino moieties of the at least two repeating charge motifs are separated by an intervening sequence of at least 32 Å, wherein the intervening sequence is neutral, and a pharmaceutically acceptable carrier.

In another aspect the invention is a pharmaceutical composition of a polypeptide of less than 50 kilodaltons having at least two repeating charge motifs, wherein the repeating charge motif is composed of a positively charged free amino moiety and a negative charge, wherein the positively charged free amino moieties of the at least two repeating charge motifs are separated by a distance of at least 8 amino acid residues and a pharmaceutically acceptable carrier.

The polymers described above encompass many types of polymers. A "polymer" as used herein is a compound having a linear backbone of individual units which are linked together by linkages. The term "backbone" is given its usual meaning in the field of polymer chemistry. The polymers may be heterogeneous in backbone composition (referred to herein as a mixed polymer), so long as they have the requisite charge motif, thereby containing any possible combination of polymer units linked together such as peptide-nucleic acids (which have amino acids linked to nucleic acids). In some cases the polymers may differ from those polymers conventionally known in the art because the polymers of the invention may have non-polymeric compounds incorporated into the backbone. For instance, the polymer of the invention may be composed entirely of amino acids except for a region which contains an organic linker that links two sets of amino acids together. In a preferred embodiment the polymers are homogeneous in backbone composition and are, for example, polypeptides, polysaccharides, and carbohydrates. A "nucleic acid" as used herein is a biopolymer comprised of nucleotides, such as deoxyribose nucleic acid (DNA) or ribose nucleic acid (RNA). A polypeptide as used herein is a biopolymer comprised of linked amino acids. A polysaccharide as used herein is a biopolymer comprised of linked sugars.

The polymers may be composed of repeating units, for instance, the entire polymer may be composed of the repeating charge motif. A "unit" is used herein consistently with its known meaning in the art to indicate a building block of a polymer, e.g., a unit of a protein is an amino acid, a unit of a nucleic acid is a nucleotide, a unit of a polysaccharide is a monosaccharide, etc. A polymer composed of repeating units is one which is composed entirely of sets of units which occur at least two times within a polymer. The repeating units of the polymer may be identical or non-identical repeating units. An "identical repeating unit" as used herein is a set of units that is repeated within the polymer and in which all of the members have the identical composition and are positioned in the identical order to the members of the other sets of units. A "non-identical repeating unit" as used herein is a set of units that is repeated within the polymer and in which all of the members do not have the identical composition and/or are not positioned in the identical order to the members of the other sets of units. Some of the members of non-identical repeating unit may have the identical order and/or position as the members of the other sets as long as all the members are not identical. When used in the context of this invention a polymer having non-identical repeating units is a polymer which may have all non-identical repeating units or a combination of identical and non-identical repeating units.

The polymers of the invention may also be composed of non-repeating units. A polymer composed of non-repeating units, as used herein, is a polymer which is not entirely composed of repeating units. For instance, a polymer composed of non-repeating units may be a random polymer. A "random" polymer is a polymer having units which have no specific or identifiable order other than the repeating charge motif. A polymer composed of non-repeating units also may be a hybrid repeat polymer which is partially random but which includes some repeating motifs.

The polymer includes at least two repeating charge motifs. A "repeating charge motif" as used herein is a motif composed of a positively charged free amino moiety and a negatively charged moiety. The motif may be composed of a dually charged single unit or of multiple units, one unit having the positive charge and a second unit having the negative charge. In the case that the charges are present on different units, the units may be adjacent to one another or may be separated by neutral units. A neutral unit is a unit which does not have a positive and/or a negative charge. The charged units of the motif may be separated by any number but preferably by less than 10 neutral units. A repeating charge motif may be present in any orientation within the polymer. For instance, in a polymer having two repeating charge motifs separated by neutral units the polymer may have the following sequence: a positive charge first followed by a negative charge, followed by neutral units followed by a negative charge and finally a positive charge. Alternatively the polymer may have the following sequence: a positive charge first followed by a negative charge, followed by neutral units followed by a positive charge and finally a negative charge, etc.

A "positively charged free amino moiety" as used herein refers to a primary amine. A "negatively charged moiety" as used herein refers to any negatively charged group but is preferably a carboxyl group. Positively charged amino acids having a free amino group include but are not limited to lysine (K), arginine (R), asparagine (N), and histidine (H). Negatively charged amino acids include but are not limited to aspartic acid (D) and glutamic acid (E).

The immunomodulating polymer has at least two repeating charge motifs but may have any number greater than two. The whole polymer, for instance, may be composed of repeating charge motifs. Alternatively the polymer may be composed of any number of repeating charge motifs between two and the number when the entire polymer is composed of repeating charge motifs (which of course will depend on the size of the polymer). The polymer may have, for instance, at least 10, 15, 20, 25, 30, 35, etc., repeating charge motifs.

The at least two repeating charge motifs are separated from one another by a minimum distance. This minimum distance is quantitated as the distance between the positively charged free amino moieties of the at least two repeating charge motifs. Alternatively the distance could be quantitated as the distance between the negatively charged moieties of the at least two repeating charge motifs. The distance, 32 Å, is equivalent to a distance of at least 8 amino acid residues of a polypeptide. A polymer having this size is composed of a minimum size corresponding to 10 amino acid residues and having the following structure, wherein each X is the positively charged free amino moiety of the repeating charge motif; and each N is independently a neutral or charged unit which could include a repeating charge motif:

$$XN_8X$$

The negatively charged moiety of the repeating unit may be on either side of the X. The formula $XN_8X$ may be the entire polymer or may be a subset of a larger polymer. The minimum distance between the positively charged free amino moieties of the at least two repeating charge motifs may be in some preferred embodiments a distance equivalent to 27, 37, 47, etc. amino acid residues, to produce polymers having minimum sizes of 30, 40, and 50 amino acid residues respectively. The polymers, of course may be larger, having additional repeating charged units or having other units at the ends.

The region between the repeating charge motif may be composed of repeating charge motifs, other units or a mixture thereof. The region may be for instance an intervening sequence that is neutral. The intervening sequence may be the same type of unit as the other units of the polymer or may be completely different. For instance, it may be a non-polymeric organic moiety.

The immunomodulating polymers of the invention are polymers having the requisite charge motif described above and which have the ability to perform any of the functions such as IL-2 induction described herein. Several specific examples of immunomodulating polymers are provided in the Examples below. In addition to the specific examples of preferred immunomodulating polymers of the invention provided herein, other preferred polymers can be identified and tested for their ability to induce secretion of IL-2 or IL-10. Polymers can be identified, for instance, in a library of compounds or synthesized de novo. These compounds can then be tested for activity in any standard IL-2 or IL-10 induction assay. Such assays are well known to those of ordinary skill in the art. For instance the in vivo RNA analysis described in Example 8 may be used or a protein analysis may be performed using the antibodies described in Example 9 or other anti-IL-2 antibodies. Additionally, in vitro assays using T cells may be used. The polymer can be added to a population of T cells in culture and production of IL-2 or IL-10 can be assessed.

The immunomodulating polymer of the invention may be derived from any source. e.g., they may be isolated and derived from natural sources such as animal or plant extracts, bacteria, fungi, seaweed and the like or synthetically prepared. For instance, when the polymer is a polypeptide it may be synthesized using conventional methods known in the art for synthesizing polypeptides. For instance, random polypeptides may be prepared according to the process disclosed in U.S. Pat. No. 3,849,550 and in Teitelbaum et al., *Eur J Immunol* 1:242 (1971). These references describe preparation of amino acids, wherein the N-carboxy-anhydrides of tyrosine, alanine, gamma-benzyl glutamate and epsilon-N-trifluoroacetyllysine are polymerised at ambient temperature in indioxane with diethylamine as initiator followed by deblocking of the gamma-carboxyl group of the glutamic acid with hydrogen bromide in glacial acetic acid and removal of the trifluoroacetyl groups from the lysine residues by 1M piperidine. Polypeptides having specific sequences and other amino acids may also be prepared using equipment and methodology that is well known in the art.

Alternatively, polypeptides may be prepared using recombinant technology. Such methods are well known in the art and have been described in many references. See, e.g., Sambrook et al., *Molecular Cloning. A Laboratory Manual*, Second Edition, Cold Spring Harbor Laboratory Press, 1989.

Additionally, the polymers may be prepared from existing (or synthetic) polymers using chemical modification of neutral units to develop the positive and negative charges. For instance, the polymers may be chemically modified according to the process disclosed in U.S. Pat. Nos. 5,700,787 and 5,679,654 for modifying polysaccharides. Briefly, the N-acetyl moiety of native polysaccharide units can be modified to yield a free amino group. Thus a polysaccharide composed of units having a negative charge and a N-acetyl group, such as *Staphylococcus aureus* type 5 capsular polysaccharide, can be modified such that each monomeric repeating unit then has both a positively and negatively charged group. For those polysaccharides that contain imine moieties (C=NH), free amino groups also can be formed by conventional chemistry techniques known to those of ordinary skill in the art. One suitable method involves the use of sodium borohydride. The imine group can be reduced with sodium borohydride to create a free amino group. This is done by adding in excess of 5 mg of borohydride to polysaccharide dissolved in distilled water while stirring at room temperature for 2 hours. The mixture is then dialyzed against water and freeze dried.

The polymer also may be chemically modified according to procedures described in Wold, F., Posttranslational protein modifications: Perspectives and prospectives, in B. C. Johnson (Ed.), *Posttranslational Covalent Modification of Proteins*, New York; Academic, 1983, pp. 1–12, for modifying polypeptides and amino acids.

Polymers useful according to the invention also may be obtained from commercial sources.

A "synthetic polymer" as used herein is a polymer which is prepared by chemical or recombinant techniques. Synthetic polymers may be but are not necessarily identical in sequence to a naturally occurring polymer.

A "non-native polymer" as used herein is a polymer that differs in composition or sequence from native naturally occurring polymers. It could not be prepared solely by isolation from natural sources without further modification.

The charge ratio of the polymer will depend on the number of positive and negative charges within the polymer and will vary depending on the polymer. In some instances when the polymer is a polypeptide it has a positive to negative charge ratio of 1:1.

The size of the polymers useful according to the invention varies greatly. Polymers between 1.2 kDa and 50 kDa will be typical, particularly for non-polysaccharide polymers. In one embodiment the polymer size is between 7 kDa and 25 kDa. In some embodiments the polymer size is between about 50 kDa and less than about 500 kDa. In yet other embodiments the polymer size is between about 500 kDa and about 5000 kDa.

The present invention provides pharmaceutical compositions, for medical use, which comprise polymers of the invention together with one or more pharmaceutically acceptable carriers and optionally other therapeutic ingredients. Thus the invention also relates to pharmaceutical compositions of the above described immunomodulating polymers in combination with an adjuvant or an antibacterial agent or other therapeutic agent and a pharmaceutically acceptable carrier. Adjuvants are discussed in more detail below.

The polymers useful in the invention may be delivered separately with another anti-bacterial antibiotic drug or in the form of anti-bacterial, antibiotic cocktails. An anti-bacterial antibiotic cocktail is a mixture of any polymer useful with this invention and an anti-bacterial antibiotic drug and/or supplementary potentiating agent. The use of antibiotics in the treatment of bacterial infection is routine. In this embodiment, a common administration vehicle (e.g., tablet, implant, injectable solution, etc.) could contain both the polymer and the anti-bacterial antibiotic drug and/or supplementary potentiating agent. Alternatively, the anti-bacterial antibiotic drug can be separately dosed.

Anti-bacterial antibiotic drugs are well known and include: penicillin G, penicillin V, ampicillin, amoxicillin, bacampicillin, cyclacillin, epicillin, hetacillin, pivampicillin, methicillin, nafcillin, oxacillin, cloxacillin, dicloxacillin, flucloxacillin, carbenicillin, ticarcillin, avlocillin, mezlocillin, piperacillin, amdinocillin, cephalexin, cephradine, cefadoxil, cefaclor, cefazolin, cefuroxime axetil, cefamandole, cefonicid, cefoxitin, cefotaxime, ceftizoxime, cefinenoxine, ceftriaxone, moxalactam, cefotetan, cefoperazone, ceftazidme, imipenem, clavulanate, timentin, sulbactam, neomycin, erythromycin, metronidazole, chloramphenicol, clindamycin, lincomycin, vancomycin, trimethoprim-sulfamethoxazole, aminoglycosides, quinolones, tetracyclines and rifampin. (See Goodman and Gilman's *Pharmacological Basis of Therapeutics*, 8th Ed., 1993, McGraw Hill, Inc.)

The precise amounts of the therapeutic agent used in combination with the polymers of the invention will depend upon a variety of factors, including the polymer selected, the dose and dose timing selected, the mode of administration, the nature of any surgery contemplated and certain characteristics of the subject. Where local administration is carried out, it will be understood that very small amounts may be required (nanograms and possibly picograms). The precise amounts selected can be determined without undue experimentation, particularly since a threshold amount will be any amount which will favorably enhance the immune response. Thus, it is believed that picogram to milligram amounts are possible, depending upon the mode of delivery, but that nanogram to microgram amounts are likely to be most useful.

The immunomodulating polymers of the invention are useful for treating IL-2-responsive disorders, protecting animals against challenge with abscess-inducing bacteria, reducing postoperative surgical adhesion formation, treating Th1 responsive disorders, treating autoimmune disease, and promoting allograft survival.

Thus the invention in one aspect is a method for inducing interleukin 2 (IL-2) secretion. This method can be performed by contacting an IL-2 secreting cell with an effective amount for inducing IL-2 secretion of a polymer of the invention. The polymer preferably is an immunomodulating polymer as described herein but wherein the polymer has non-repeating units. In another preferred embodiment the polymer is an immunomodulating polysaccharide as described herein of repeating or non-repeating units.

The invention is based in part on the discovery that the immunomodulating polymers having at least two positive and two negative groups cause induction of IL-2. IL-2 is a cytokine which is well known to those of ordinary skill in the art and exerts a variety of physiological effects.

An IL-2 secreting cell is any cell which produces IL-2 in response to activation with the non-polysaccharide polymer of the invention. These cells include, for instance, T lymphocytes, including CD4+ Th1 and CD4+ Th2 cells and CTL's (CD8+). The IL-2 secreting cell is contacted with an effective amount of the polymer for inducing IL-2 secretion. An effective amount for inducing IL-2 secretion is that amount which results in any induction in IL-2 secretion. If the IL-2 secreting cell, for instance, is not secreting any IL-2 at the time that it is contacted with the polymer, then the ability of the polymer to induce any IL-2 is an effective amount of the polymer. If the IL-2 secreting cell is already producing IL-2, then the ability of the polymer to increase that amount is also an effective amount of the polymer.

There are many instances in which it is desirable to induce IL-2. It is desirable to induce IL-2, for instance, in vitro for a variety for experimental assays. An example of such an assay is an assay for identifying compounds useful for blocking IL-2 induction. Other assays include physiological assays for determining the effects of IL-2 on various systems. It is also desirable to induce IL-2 in a variety of ex vivo/in vivo conditions. It is known, for instance, that IL-2 is useful for the treatment of AIDS, renal cell carcinoma, and melanoma.

Thus the invention also encompasses a method for treating an IL-2-responsive disorder by inducing IL-2 secretion. A subject having an IL-2-responsive disorder is administered an effective amount for inducing IL-2 secretion of an immunomodulating polymer of the invention. The subject having an IL-2-responsive disorder is one who is not preparing to undergo surgery and who has or is at risk of developing AIDS, renal cell carcinoma, or melanoma.

In another aspect of the invention, a method for inducing protection against abscess formation associated with infection is provided. The method includes the step of administering to a subject in need of such protection a pharmaceutical preparation containing an effective amount for inducing protection against abscess formation of IL-2, an IL-2 inducing compound, or the immunomodulating polymer of the invention. It was discovered according to the invention that exogenously administered IL-2 and compounds which induce IL-2 are capable of inducing protection against abscess formation. The finding is particularly surprising in view of the prior art teaching that IL-2 may participate in abscess formation. This teaching was based on the discovery that antibodies specific for IL-2 can help block abscess formation. Surprisingly, it was discovered according to the invention that IL-2 and compounds which induce IL-2 actually protect against abscess formation in vivo.

An IL-2-inducing compound as used herein is any compound which induces IL-2 secretion by an IL-2 secreting cell. These compounds include, but are not limited to superantigen (e.g., SEA), an anti-CD3 antibody, an oxidative chemical, tucaresol, and an activated T cell.

The polymers of the invention not only induce the secretion of IL-2, as an initial step, but also subsequently induce the secretion of IL-10. Without meaning to be bound to any particular theory or mechanism, it is believed that the secretion of IL-10, which is observed following administration of the polymers of the invention, is indirect, i.e., mediated by effects arising as a result of the IL-2 secretion. IL-10 is a cytokine which is well known to those of ordinary skill in the art and exerts a variety of physiologic effects. It is considered to be a key Th2 cytokine which is known to inhibit Th1 function, including production of IL-2. IL-10 has been shown by others to prevent many types of inflammatory processes such as sepsis, inflammatory bowel diseases, and adhesions. In addition, IL-10 prevents certain autoimmune diseases, graft-versus-host disease (GvHD), and psoriasis.

The immunomodulating polymers useful for protecting against abscess formation are the immunomodulating polymers of the invention described herein but wherein the polymer has non-repeating units. Other immunomodulating polymers useful for protecting against abscess formation are the immunomodulating polypeptides of the invention described herein.

The compounds are administered in an effective amount for inducing protection against abscess formation. An effective amount for inducing protection against abscess formation as used herein is that amount of IL-2, an IL-2 inducing compound or an immunomodulating polymer of the invention that will, alone or together with further doses or additional therapeutic compounds, inhibit or prevent the formation of abscess resulting from infection by a particular bacteria. It is believed that doses ranging from 1 nanogram/kilogram to 100 milligrams/kilogram, depending upon the mode of administration, will be effective. The preferred range is believed to be between 500 nanograms and 500 micrograms/kilogram, and most preferably between 1 microgram and 100 micrograms/kilogram. The absolute amount will depend upon a variety of factors (including whether the administration is in conjunction with elective surgery or emergency surgery, concurrent treatment, number of doses and individual patient parameters including age, physical condition, size and weight) and can be determined with no more than routine experimentation. It is preferred generally that a maximum dose be used, that is, the highest safe dose according to sound medical judgment.

Multiple doses of the pharmaceutical compositions of the invention are contemplated. The invention has been shown to be effective with multiple doses administered over a three week period preceding surgery, over a two week period preceding surgery, over a one week period preceding surgery, when the first dose was administered only 24 hours preceding surgery, and even when given only after exposure to bacteria. Further doses may be administered after surgery as well. Any regimen that results in an enhanced immune response to bacterial infection/contamination and subsequent abscess formation may be used, although optimal doses and dosing regimens are those which would not only inhibit the development of abscess formation, but also would result in a complete protection against abscess formation by a particular bacterial organism or a variety of bacterial organisms. Desired time intervals for delivery of multiple doses of a particular polymer can be determined by one of ordinary skill in the art employing no more than routine experimentation.

Thus, in one aspect the invention is useful whenever it is desirable to prevent bacterial abscess formation in a subject. This includes prophylactic treatment to prevent such conditions in planned surgical procedures as well as emergency situations. Elective surgeries include the following intraabdominal surgeries: right hemicolectomy; left hemicolectomy;

sigmoid colectomy; subtotal colectomy; total colectomy; laparoscopic or open cholecystectomy; gastrectomy; etc. Emergency surgeries include those to correct the following conditions: perforated ulcer (duodenal or gastric); perforated diverticulitis; obstructive diverticulitis; acute appendicitis; perforated appendicitis; blunt abdominal trauma; penetrating abdominal trauma; second operation to drain abscess; etc. The invention also is useful with nonintraabdominal surgeries such as cardiac surgeries and surgeries to correct wound infections. The invention also is useful in connection with diseases that predispose a subject to abscess formation such as pelvic inflammatory disease, inflammatory bowel disease, urinary tract infections and colon cancer. The invention thus is useful with abscesses of virtually any tissue or organ, including specifically but not limited to dermal abscesses such as acne. Those of ordinary skill in the art to which this invention pertains will recognize the range of conditions and procedures with which the invention is useful. A subject as used herein means: humans, primates, horses, cows, sheep, pigs, goats, dogs, cats, and rodents.

When administered to prevent abscess formation, the immunomodulating polymers of the invention may be administered with an adjuvant. The term "adjuvant" includes any substance which is incorporated into or administered simultaneously with the polymer and which potentiates the immune response in the subject. Adjuvants include aluminum compounds, e.g., gels, aluminum hydroxide and aluminum phosphate, and Freund's complete or incomplete adjuvant (in which the polymer is incorporated in the aqueous phase of a stabilized water in paraffin oil emulsion). The paraffin oil may be replaced with different types of oils, e.g., squalene or peanut oil. Other materials with adjuvant properties include BCG (attenuated *Mycobacterium tuberculosis*), calcium phosphate, levamisole, isoprinosine, polyanions (e.g., poly A:U), lentinan, pertussis toxin, lipid A, saponins, peptides (e.g., muramyl dipeptide) and rare earth salts (e.g., lanthanum and cerium). The amount of adjuvant depends on the subject and the particular polymer used and can be readily determined by one skilled in the art without undue experimentation. Preferred adjuvants are those that selectively stimulate T cells. It is desirable to avoid adjuvants that might suppress a T cell response.

In another aspect of the invention, a method is provided for inducing protection against postoperative surgical adhesion formation associated with many common types of surgery. The method includes the step of administering to a subject in need of such protection a pharmaceutical preparation containing an effective amount for reducing postoperative surgical adhesion formation of the immunomodulating polymer of the invention. It was discovered according to the invention that administration of the polymer at a site separate from the operative site is capable of inducing protection against postoperative surgical adhesion formation. The finding is particularly surprising in view of the prior art teaching that local administration of certain polymers into the surgical site is effective for reducing the incidence of postoperative surgical adhesion. Surprisingly, it was discovered according to the invention that polymers of the invention can be effective when given subcutaneously apart from the surgical site at which adhesions are likely to form.

The immunomodulating polymers useful for protecting against postoperative surgical adhesion formation are the immunomodulating polymers of the invention described. Other immunomodulating polymers useful for protecting against abscess formation are the immunomodulating polypeptides of the invention described herein.

The compounds are administered in an effective amount for inducing protection against postoperative surgical adhesion formation. An effective amount for inducing protection against postoperative surgical adhesion formation as used herein is that amount of an immunomodulating polymer of the invention that will, alone or together with further doses or additional therapeutic compounds, inhibit or prevent the formation of postoperative surgical adhesion. It is believed that doses ranging from 1 nanogram/kilogram to 100 milligrams/kilogram, depending upon the mode of administration, will be effective. The preferred range is believed to be between 500 nanograms and 500 micrograms/kilogram, and most preferably between 1 microgram and 100 micrograms/kilogram. The absolute amount will depend upon a variety of factors (including whether the administration is in conjunction with elective surgery or emergency surgery, concurrent treatment, number of doses and individual patient parameters including age, physical condition, size and weight) and can be determined with routine experimentation. It is preferred generally that a maximum dose be used, that is, the highest safe dose according to sound medical judgment.

Multiple doses of the pharmaceutical compositions of the invention are contemplated. The invention has been shown to be effective with multiple doses administered over a three day period beginning on the day preceding surgery. Further doses may be administered post surgery as well. Any regimen that results in a reduced postoperative surgical adhesion formation may be used, although optimum doses and dosing regimens are those which would not only inhibit the development of postoperative surgical adhesion formation, but also would result in a complete protection against postoperative surgical adhesion formation. Desired time intervals for delivery of multiple doses of a particular polymer can be determined by one of ordinary skill in the art employing no more than routine experimentation.

Thus, in one aspect the invention is useful whenever it is desirable to prevent postoperative surgical adhesion formation in a subject. This includes prophylactic treatment to prevent adhesion formation following planned surgical procedures as well as following emergency operations. Elective surgeries include the following intraabdominal surgeries: right hemicolectomy; left hemicolectomy; sigmoid colectomy; subtotal colectomy; total colectomy; laparoscopic or open cholecystectomy; gastrectomy; pancreatectomy; splenectomy; liver, pancreas, small bowel, or kidney transplantation; lysis of adhesions; etc. Emergency intraabdominal surgeries include those to correct the following conditions: perforated ulcer (duodenal or gastric); perforated diverticulitis; obstructive diverticulitis; bowel obstruction; acute appendicitis; perforated appendicitis; blunt abdominal trauma; penetrating abdominal trauma; second operation to drain abscess; ruptured abdominal aortic aneurysm, etc. The invention also is useful with nonintraabdominal surgeries such as cardiac surgeries, open and endoscopic orthopedic surgeries, neurosurgeries, gynecologic and pelvic surgeries, and surgeries to correct wound infections. The invention also is useful in connection with diseases that predispose a subject to spontaneous adhesion formation such as pelvic inflammatory disease, inflammatory bowel disease, urinary tract infections and colon cancer. The invention thus is useful with inflammatory processes involving virtually any tissue or organ. Those of ordinary skill in the art to which this invention pertains will recognize the range of conditions and procedures with which the invention is useful.

When administered to prevent postoperative surgical adhesion formation, the polymers of the invention may be administered either distant from the operative site, including systemically, or locally into the operative site at which it is desirable to reduce the likelihood of postoperative surgical adhesion formation. The polymers of the invention can be administered as aqueous solutions, as crosslinked gels, or as any temporal or physical combination of aqueous solution and crosslinked gel forms. Crosslinked gels must retain the repeating charge motif, namely, the positively charged free amino moiety and a negatively charged moiety, to an extent sufficient for the purpose of reducing or preventing postoperative surgical adhesion formation according to the invention.

Because the polysaccharide polymers of the invention are zwitterionic and include a positively charged free primary amino group in each of the at least two repeating charge motifs, the polysaccharide polymers of the invention can include deacetylated hyaluronic acid, deacetylated chondroitin sulfate, deacetylated keratan sulfate, and deacetylated dermatan sulfate. For the same reasons, the polysaccharide polymers of the invention do not include N,O-carboxymethylchitosan (NOCC), hyaluronic acid (HA) or hyaluronate salts (including, for example, sodium hyaluronate, potassium hyaluronate, magnesium hyaluronate, and calcium hyaluronate), carboxymethylcellulose (CMC), dextran sulfate, pentosan (poly)sulfate, dermatan sulfate, chondroitin sulfate, keratan sulfate, heparan sulfate, heparin, or polyvinylpyrrolidone (PVP). In some preferred embodiments the polymer is a polypeptide.

It has been discovered that certain polymers can be used to stimulate host T cells and induce protection against numerous bacteria. This protective effect is T-cell-dependent and not mediated by a humoral antibody response. As such, administration of the preparations of the invention is not "vaccination" and the preparations are not "vaccines" which mediate protection that is specific to bacteria expressing the immunizing antigen.

It was also found according to the invention that the immunomodulating polymers described above are useful for activating T cells to produce Th1 cytokines. The T cell is contacted with an effective amount for inducing IL-2 secretion of the immunomodulating polymer of the invention. It was discovered, as demonstrated in the examples below, that the immunomodulating polymer activates T cells causing secretion of Th1 specific cytokines, such as IL-2 and interferon-γ (IFN-γ). When T cells are stimulated, they can differentiate toward either Th1 or Th2 cytokine production. The invention in this aspect is based on the discovery that the immunomodulating polymers of the invention can activate T cells to mediate cytokine release having a profile of Th1 cytokines and thus useful any time it is desirable to activate T cells to produce a Th1 cytokine profile.

While not intending to be bound by any particular theory, it is believed that the immunomodulating polymers of the invention activate T lymphocytes to produce a Th1 cytokine profile, resulting in the release of IL-2. IL-2 then functions to protect against abscess formation by blocking the growth of bacteria or preventing or inhibiting other disorders mediated by IL-2. As was demonstrated in the examples below, immunomodulating polymers, T cells activated by the immunomodulating polymers, extracts of the activated T cells and exogenous IL-2 all function in vivo to induce protection against abscess formation. In this manner, the invention provides methods for protecting against abscess formation by the administration of each of these materials.

Thus the invention encompasses a method of activating T cells. The method involves contacting a T cell in the presence of an antigen presenting cell with an effective amount for inducing IL-2 secretion of an immunomodulating polymer of the invention. Preferably the polymer has non-repeating units. In another preferred aspect the polymer is an immunomodulating polypeptide of the invention which has repeating or non-repeating units.

A "T cell" as used herein is a thymus-derived lymphocyte characterized in part by the expression on its cell surface of CD3 and a T cell antigen receptor. A "Th1 cell" as used herein is a CD4+ T lymphocyte that secretes principally IL-2, IFN-γ, and lymphotoxin. A Th1 cytokine profile includes IL-2, IFN-γ, and lymphotoxin.

The invention also encompasses methods for treating a Th1-cell-responsive disorder by activating a T cell to produce Th1-cell-specific cytokines. The method is accomplished by administering to a subject having a Th1-cell-responsive disorder an effective amount for inducing IL-2 secretion by the T cell an immunomodulating polymer of the invention. A subject having a Th1-cell-responsive disorder is a subject who is not preparing to undergo surgery but who is at risk of developing or has a Th1-cell-responsive disorder. A "Th1-cell-responsive disorder" is an immune-mediated disorder which is inhibited with Th1 cytokines. A disorder is inhibited as used herein if the development of disorder is partially or completely prevented or if the magnitude of the disorder is reduced. Th1-cell-responsive disorders include but are not limited to insulin-dependent diabetes mellitus, experimental allergic encephalomyelitis, inflammatory bowel disease, and allograft rejection.

It was also discovered according to the invention that certain immunomodulating polymers of the invention are useful for suppressing IgG antibody response to specific antigen and also to promote allograft survival. The immunomodulating polymers useful according to these aspects of the invention include the polymers discussed above except for those which are composed of alanine, glutamic acid, lysine, and tyrosine in a molar ratio of approximately 6:2:5:1 or in a ratio of 4–6:1.4–2.1:3.2–4.2:1, 6:2:4.5:1, 4.1–5.8:1.4–1.8:3.2–4.2:1, 6:1.9:4.7:1, 4.9:1.7:3.8:1, or 6:1.8:4:1. In general the polymer, when composed only of glutamic acid, lysine, alanine, and tyrosine specifically excludes those forms of GLAT and copolymer 1 described in the literature. In some embodiments the immunomodulating polymers of the invention are useful for treating these disorders in a subject that is not preparing to undergo surgery.

A "disorder characterized by an inappropriate IgG antibody response to specific antigen" as used herein is a disorder such as acute glomerulonephritis, Goodpasture's syndrome, certain autoimmune arthritidies including rheumatoid arthritis, systemic lupus erythematosus (lupus), AIDS, Sjögren's syndrome, autoimmune hemolytic anemia, idiopathic thrombocytopenic purpura (ITP), and certain forms of thyroiditis.

The polymers are also useful for promoting allograft survival. The term "promoting allograft survival" as used herein denotes the clinically measurable extension or preservation of physiologically useful function of transplanted cells, tissues, or organs derived from another individual of the same species as the recipient, beyond the corresponding function of similar transplants in untreated recipients.

The polymers of the present invention have adjuvant properties by themselves. To the extent that the polymers described herein potentiate human immune responses, they can be used as adjuvants in combination with other materials.

The preparations of the invention are administered "in conjunction with" infection, meaning close enough in time with the surgery, trauma or diseases that predispose the host to abscess formation so that a protective effect against abscess formation is obtained. The preparations may be administered long before surgery in the case of elective surgery (i.e., weeks or even months) preferably with booster administrations closer in time to (and even after) the surgery. Particularly in emergency situations, the preparations may be administered immediately before (minutes to hours) and/or after the trauma or surgery. It is important only that the preparation be administered close enough in time to the surgery so as to enhance the subject's immune response against bacterial infection/contamination, thereby increasing the chances of a successful host response and reducing the likelihood of abscess formation.

The formulations of the invention are administered in pharmaceutically acceptable solutions, which may routinely contain pharmaceutically acceptable concentrations of salt, buffering agents, preservatives, compatible carriers, adjuvants, and optionally other therapeutic ingredients.

The polymer may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts can be prepared as alkaline metal or alkaline earth salts, such as sodium, potassium or calcium salts of the carboxylic acid group.

Suitable buffering agents include: acetic acid and a salt (1–2% w/v); citric acid and a salt (1–3% w/v); boric acid and a salt (0.5–2.5% w/v); and phosphoric acid and a salt (0.8–2% w/v). Suitable preservatives include benzalkonium chloride (0.003–0.03% w/v); chlorobutanol (0.3–0.9% w/v); parabens (0.01–0.25% w/v) and thimerosal (0.004–0.02% w/v).

The pharmaceutical compositions of the invention contain an effective amount of a polymer optionally included in a pharmaceutically acceptable carrier. The term "pharmaceutically acceptable carrier" means one or more compatible solid or liquid filler, dilutants or encapsulating substances which are suitable for administration to a human or other animal. The term "carrier" denotes an organic or inorganic ingredient, natural or synthetic, with which the active ingredient is combined to facilitate the application. The components of the pharmaceutical compositions also are capable of being commingled with the polymers of the present invention, and with each other, in a manner such that there is no interaction which would substantially impair the desired pharmaceutical efficiency.

Compositions suitable for parenteral administration conveniently comprise sterile aqueous preparations, which can be isotonic with the blood of the recipient. Among the acceptable vehicles and solvents are water, Ringer's solution, and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid find use in the preparation of injectables. Carrier formulations suitable for subcutaneous, intramuscular, intraperitoneal, intravenous, etc. administrations may be found in Remington's Pharmaceutical Sciences, Mack Publishing Company, Easton, Pa.

The polymers useful in the invention may be delivered in mixtures of more than one polymer. A mixture may consist of several polymers.

A variety of administration routes are available. The particular mode selected will depend, of course, upon the particular polymer selected, the particular condition being treated and the dosage required for therapeutic efficacy. The methods of this invention, generally speaking, may be practiced using any mode of administration that is medically acceptable, meaning any mode that produces effective levels of an immune response without causing clinically unacceptable adverse effects. Preferred modes of administration are parenteral routes. The term "parenteral" includes subcutaneous, intravenous, intramuscular, or intraperitoneal injection or infusion techniques.

The compositions may conveniently be presented in unit dosage form and may be prepared by any of the methods well known in the art of pharmacy. All methods include the step of bringing the polymer into association with a carrier which constitutes one or more accessory ingredients. In general, the compositions are prepared by uniformly and intimately bringing the polymer into association with a liquid carrier, a finely divided solid carrier, or both, and then, if necessary, shaping the product. The polymer may be stored lyophilized.

Other delivery systems can include time-release, delayed release or sustained release delivery systems. Such systems can avoid repeated administrations of the anti-inflammatory agent, increasing convenience to the subject and the physician. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono-, di-, and tri-glycerides; hydrogel release systems; silastic systems; peptide based systems; wax coatings; compressed tablets using conventional binders and excipients; partially fused implants; and the like. Specific examples include, but are not limited to: (a) erosional systems in which an agent of the invention is contained in a form within a matrix such as those described in U.S. Pat. Nos. 4,452,775, 4,675,189, and 5,736,152, and (b) diffusional systems in which an active component permeates at a controlled rate from a polymer such as described in U.S. Pat. Nos. 3,854,480, 5,133,974 and 5,407,686. In addition, pump-based hardware delivery systems can be used, some of which are adapted for implantation.

EXAMPLES

Example 1

Sources of Bacteria, Isolation and Modification of Polysaccharides, and Animal Model for Intraabdominal Sepsis

*B. fragilis* NCTC 9343 and ATCC 23745 were originally obtained from the National Collection of Type Cultures (London, England) or the American Type Culture Collection (Bethesda, Md.). Microorganisms were stored at −80° C. in peptone-yeast or brain heart infusion broth until used, and grown anaerobically as previously described. Pantosti et al. *Infect Immun* 59:2075 (1991). The CPC from *B. fragilis* NCTC 9343 or ATCC 23745 was isolated by hot phenol/water extraction and subsequent purification of PS A performed as previously described. Tzianabos, A et al. *J Biol Chem* 267:18230 (1992).

The *S. pneumoniae* type I capsular polysaccharide (CP) and other pneumococcal polysaccharides were obtained from the ATCC (MD).

Chemical modifications of polysaccharides to produce molecules with altered charges have been described previously. Taylor, R et al. *Biochemistry* 11:1383 (1972) (carbodiimide reduction) and Baumann, H et al. *Biochemistry* 31:4081 (1992) (N-acetylation and deamination).

The rat model of intraabdominal sepsis used in this study has been described previously. Onderdonk, A et al. *J Infect Dis* 136:82 (1977) and Tzianabos, A et al. *Science* 262:416 (1993). Briefly, male Wistar or Lewis rats (Charles River Laboratories, Wilmington, Mass.) weighing between 180 and 200 g were housed separately and received chow (Ralston Purina, St. Louis. MO) and water ad libitum. Animals were anesthetized with a single intraperitoneal injection of 0.15 ml of Nembutal (50 mg/ml; Abbott Laboratories, North Chicago, Ill.), and their abdomens were shaved and swabbed with a tincture of iodine. An anterior midline incision (0.5–1.0 cm) was made through the abdominal wall and peritoneum, and a gelatin capsule containing 0.5 ml of inoculum was inserted into the pelvis. The inoculum contained either *B. fragilis* NCTC 9343 ($10^8$ cfu/animal), *S. aureus* PS 80 ($10^7$ cfu/animal), or purified test polysaccharide, mixed 1:1 with an adjuvant solution containing sterile rat cecal contents and 10% barium sulfate (w/v) as previously described. Onderdonk, A et al. *Infect Immun* 13:22 (1976). The incisions were closed with interrupted 3.0 silk sutures, and the animals were returned to the cages.

Six days later animals were necropsied in a blinded fashion and examined for the formation of one or more intraabdominal abscesses by an observer blinded to the experimental groups. Rats that possessed one or more fully formed abscesses were scored as positive. Animals that did not have any fully formed abscesses were scored as negative.

Example 2

T Cell Activation by PS A Depends on Charge Motif

The ability of *B. fragilis* PS A to elicit a protective host response that is dependent on T cells suggested an interaction between PS A and this cell type. Thus experiments were performed to determine whether PS A activates T cells in vitro.

T cell proliferation assays were performed on cells obtained from human leukopacs (discarded white cells from anonymous platelet donors). Mononuclear cells were separated by ficoll-hypaque sedimentation to eliminate red cells and polymorphonuclear leukocytes. The mononuclear layer, which consisted of T cells, B cells, and mononuclear cells, was depleted of B cells and monocytes by passage over nylon wool column. A portion of these cells was saved prior to placement on nylon wool and were used as autologous feeder cells following irradiation with 6.4 kRads with a cesium source for 4.8 min. Nylon passed cells which were greater than 98% CD3 positive (as determined by FACS analysis) were used as responder cells or further depleted with antibodies to CD4 (OKT4) or CD8 (OKT8) followed by negative selection with magnetic beads. Finberg, R W et al. *J Immunol* 149:2055 (1992); Haregewoin, A et al. *Nature* 340:309 (1989). Ten-fold dilutions of PS A were added to human T cells ($5 \times 10^4$ cells/200 µl) co-cultured with irradiated APCs ($2.5 \times 10^5$/200 µl) for 12 days in U-bottom 96 well plates (Corning-Costar Corp., Cambridge, Mass.) with RPMI 1640 and 5% fetal calf serum. Nguyen, L H et al. *J Virol* 66:7067 (1992). At predetermined time points, cells were pulsed with 1 mCi of $^3$H-thymidine/well 6 h prior to harvest in order to measure cell proliferation. Cells were washed extensively, harvested, and the amount of radioactive uptake counted by liquid scintillation. The response to PS A typically varied with human T cell donors. In all assays, irradiated APCs cultured with PS A or SEA alone did not proliferate in response to these antigens. Data were expressed as the average of triplicate wells ± the standard error of cpm represented. For all proliferation experiments, data represent typical results from at least five different experiments.

Figure 2:
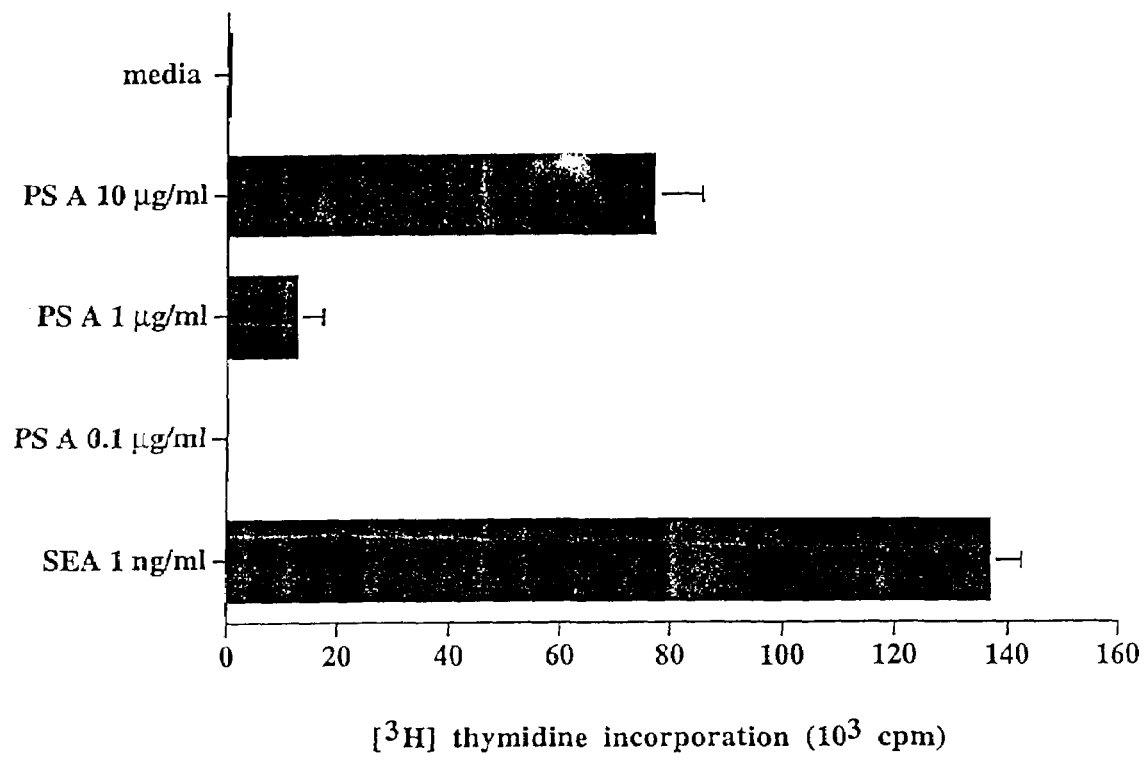
FIG. 2. T cell proliferation in response to B. fragilis PS A. Human T cells ($5 \times 10^4$ cells/ml) were co-cultured with irradiated APCs ($2.5 \times 10^5/200$ µl) for 12 days in the presence of 10-fold dilutions of PS A or staphylococcal enterotoxin A (SEA) at 1 ng/ml as a positive control. $^3$H thymidine (1 µCi/well) was added during the last 6 hours of culture. The response to PS A was dose-dependent and peaked six days after culture. The results shown are representative of at least five independent experiments.

In proliferation assays with human T cells, PS A elicited a dose-dependent response (dose range: 10 to 0.1 µg/ml, FIG. 2). This proliferative response peaked 6 days after culture with PS A. When tested at an optimal concentration of 1 ng/ml, the proliferative response to staphylococcal enterotoxin A (SEA) also peaked at day 6 and yielded stimulation indices ranging from 50- to 150-fold greater than the media control (FIG. 2).

Figure 3:
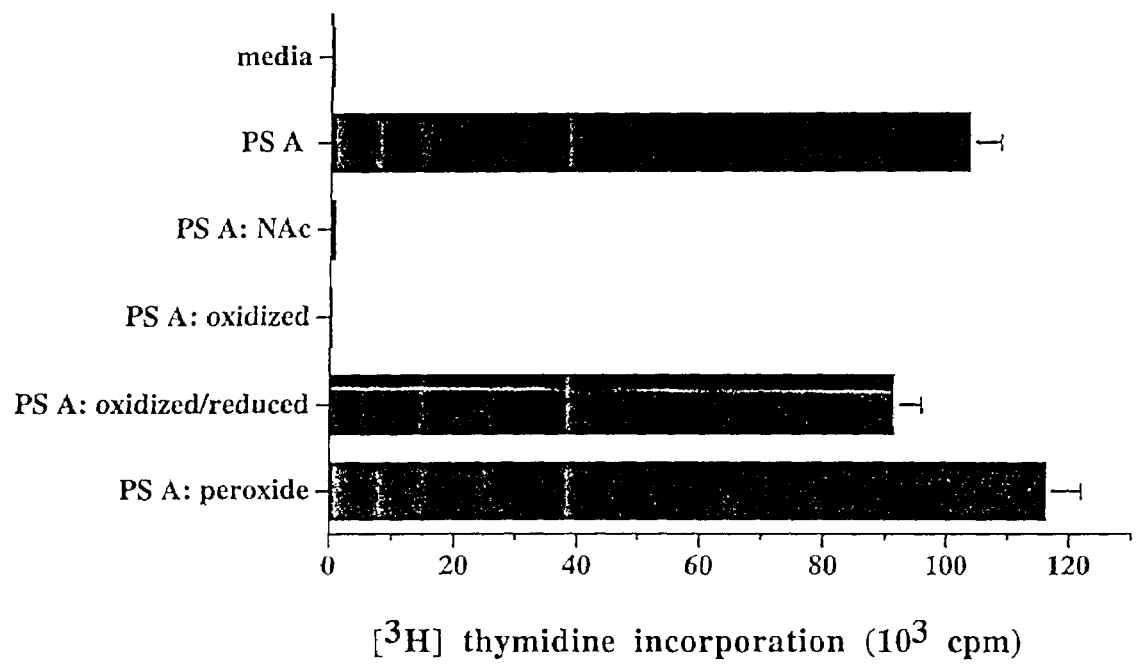
FIG. 3. T cell proliferation in response to B. fragilis PS A and modified PS A derivatives. All polysaccharides were tested at a concentration of 10 µg/ml. CD4+ T cells were used as the responder cell in this system. PS A was chemically N-acetylated by treatment with acetic anhydride as described in FIG. 1, Modification I. Conversion of the free amino groups of PS A to N-acetyl groups abrogated the proliferative response (PS A:NAc). Reduction of the negatively charged carboxyl group associated with the pyruvate ketal ring of the terminal galactose residue (FIG. 1, Modification II) reduced the proliferative response by 72%. PS A was subject to selective oxidation by treatment with 0.01M sodium metaperiodate (FIG. 1, Modification III). Oxidation by this periodate method abrogated T cell activation by this polysaccharide (PS A: oxidized). However, upon reduction of the oxidized PS A with $NaBH_4$ (FIG. 1, Modification IV), the proliferative response to PS A was regenerated (PS A: oxidized/reduced). Demonstration of comparable proliferative activity by the peroxide-oxidized PS A (PS A: peroxide) and regeneration of the proliferative activity of the periodate-oxidized and reduced PS A confirmed that the observed T cell response is attributable to the polysaccharide and not to a contaminating protein.

We have demonstrated the importance of the free amino group at C4 of the 2-acetamido-4-amino-2,4,6-trideoxygalactose residue of PS A (Sugar 1, FIG. 1) and the carboxyl group associated with the pyruvate group on Sugar 3 in mediating in vivo biologic functions. Tzianabos, A O et al. *Science* 262:416 (1993); Tzianabos, A. O. et al. *Infect Immun* 62:4881 (1994); Tzianabos, A O et al. *Infect Immun* 62:3590 (1994). Additionally, the role of these chemical groups on T cell activation by PS A was assessed. A specific chemical modification converted the free amino groups on PS A to neutral N-acetyl groups (FIG. 1. Modification I). N-acetylation of PS A abrogated T cell activation by PS A, a result indicating that free amino groups on PS A are critical for T cell activation (FIG. 3, 10 µg/ml each of PS A vs. PS A:NAc). Chemical modification of the negatively charged group on PS A via carbodiimide reduction of the pyruvate substituent associated with the terminal galactose residue (FIG. 1, Modification II) resulted in a 72% decrease in the proliferative response as compared with the unmodified PS A (7,937±3264 cpm versus 27,886±7890 cpm, respectively). These data illustrate the important role of these charged groups in mediating T cell activation in vitro and correlates with the impact of these groups on PS A-mediated protection against abscess formation in vivo. Tzianabos, A O et al. *Infect Immun* 62:4881 (1994).

The following data specifically address the possibility that the T cell proliferative response to PS A could reflect the presence of protein or peptide contamination: (1) Purification of surface polysaccharides from *B. fragilis* involved procedures designed to degrade or denature proteins (extraction with hot phenol, repeated pronase digestion, and boiling in 1M NaOH for 1 h). Pantosti, A et al. *Infect Immun* 59:2075 (1991). (2) SDS-PAGE, quantitative protein assays, and amino acid analysis reflected the absence of protein in polysaccharide samples. (3) Due to its charge motif, PS A ionically aggregates in aqueous solution, causing PS A to lose its ability to stimulate T cell proliferation. It is important to disaggregate this ionic complex via isoelectric focusing shortly before use for T cell activation to occur. (4) Chemical treatment of PS A, which specifically alters carbohydrates but not proteins, abrogated proliferation by PS A. However, chemical regeneration of the affected carbohydrate groups restored T cell activation. For the last set of experiments, PS A was chemically oxidized by sodium metaperiodate ($NaIO_4$) treatment which is selective for the cleavage of the C—C bond between vicinal hydroxyl groups on carbohydrates. In the case of PS A, periodate oxidation is exquisitely specific for removing the C6 of the galactofuranose side chain (FIG. 1, Sugar 4, Modification III), creating an aldehyde group at C5. When tested for T cell proliferation, periodate-oxidized PS A failed to elicit a response (FIG. 3, 10 µg/ml each PS A vs. PS A:oxidized). Loss of activity is likely due to the generation of aldehydes following periodate oxidation that interact with free amino groups on PS A to form intermediate Schiff bases. The occupation of free amino groups with intra- and inter-molecular aldehydes in Schiff base formation rather than in the interaction with T cells and/or APCs may have resulted in the lack of proliferation by the oxidized form of PS A. Rhodes has shown that Schiff base formation between T cells and APCs are critical in providing signals for T cell activation. Zheng, B et al. *Science* 256:1560 (1992).

After periodate oxidation, PS A was reduced with sodium borohydride ($NaBH_4$), converting the aldehyde group at C5 to a hydroxymethyl group (FIG. 1, Modification IV). This modification resulted in the conversion of the side-chain sugar to an arabinofuranose residue but left the original motif of the charged groups on the polysaccharide intact. The regeneration of the side-chain hydroxymethyl group on oxidized PS A restored the proliferative activity of this polysaccharide (FIG. 3, 10 µg/ml each PS A vs. PS A:oxidized/reduced). NMR spectroscopy and GC-MS confirmed that 100% of the repeating units were modified as described.

Generally, proteins are highly resistant to $NaIO_4$ oxidation, however it is possible that this treatment could oxidize thiol groups present in cysteine residues associated with proteins or peptides to sulfoxide derivatives. J. March, *Advances in Organic Chemistry* (John Wiley and Sons, New York, 4th ed., 1992). If this were the case, reduction with $NaBH_4$ could reverse the oxidation procedure to regenerate this affected amino acid. Therefore, the results described above might be attributed to contamination by peptides containing cysteines. To eliminate this remaining possibility, PS A was treated with hydrogen peroxide, which oxidizes thiol groups on cysteine to sulfoxide derivatives but does not affect carbohydrate structure. J. March, *Advances in Organic Chemistry* (John Wiley and Sons, New York, 4th ed., 1992). T cell proliferation assays with hydrogen peroxide-treated PS A revealed that the proliferative activity was equivalent to that of the untreated polysaccharide (FIG. 3, 10 µg/ml each PS A vs. PS A:peroxide). Therefore, demonstration of comparable proliferative activity by the peroxide-oxidized product and recovery of proliferative activity via $NaBH_4$ reduction of periodate-oxidized PS A confirmed that the observed T cell response is attributable to the carbohydrate and not to a contaminating protein.

Example 3

Characterization of Zwitterionic Polymer Charge Motif Responsible for T Cell Activation This example examines whether another bacterial polysaccharide with a charge motif similar to PS A could activate T cells in vitro. *Streptococcus pneumoniae* type 1 capsular polysaccharide (CP) is among the few naturally occurring polysaccharides that have oppositely charged groups. Lindberg, B et al. *Carhohydr Res* 78:111 (1980). The type 1 CP is a trisaccharide repeating unit that has the same sugar residue with a positively charged free amino group (2-acetamido-4-amino-2,4,6-trideoxygalactose residue) that occurs in PS A. In addition, the type I CP has two galacturonic acid residues containing negatively charged carboxyl groups per repeating unit. In previous studies, we have demonstrated that like PS A, the type I CP also protects animals against abscess formation. Tzianabos, A O et al. *Infect Immun* 62:4881 (1994). In addition, this protective activity is also dependent on the presence of the free amino group on its repeating unit structure. *S. pneumoniae* type 3 CP differs from the type 1 CP in that it is a disaccharide repeating unit of glucose and glucuronic acid. Reeves, R E et al. *J Biol Chem* 139:511 (1941).

*Streptococcus pneumoniae* type 1 and type 3 capsular polysaccharides were obtained from the ATCC (Rockville, Md.), and treated with 2M NaOH for 1 hour at 80° C. to remove contaminating cell wall polysaccharide, C substance. Following purification by gel filtration chromatography, the *S. pneumoniae* polysaccharides were subjected to isoelectric focusing, dialyzed, lyophilized and stored in 3M NaCl to prevent aggregation. T cell proliferation assays were performed as described in Example 2 above, substituting type 1 or type 3 CP for PSA.

Figure 4:
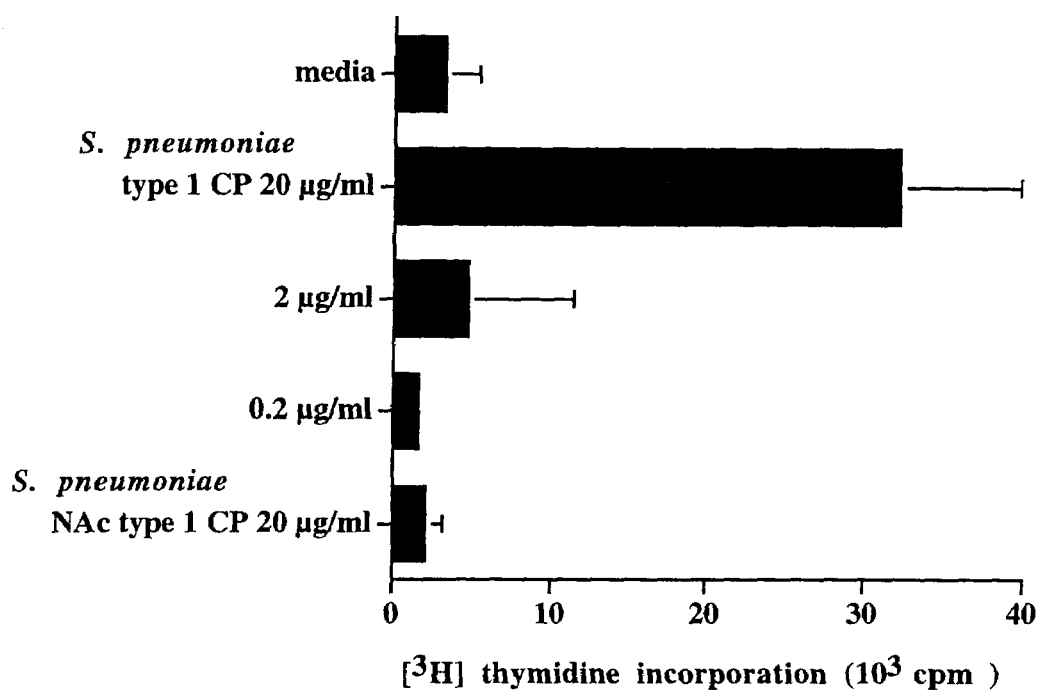
FIG. 4. T cell dose response and effect of N-acetylation of the S. pneumoniae type 1 capsular polysaccharides (CP). The type 1 CP elicited a potent T cell response that was typically 60–70% of the PS A response. N-acetylation of type 1 capsular polysaccharide abrogated T cell proliferation (NAc type 1 CP).
Figure 5:
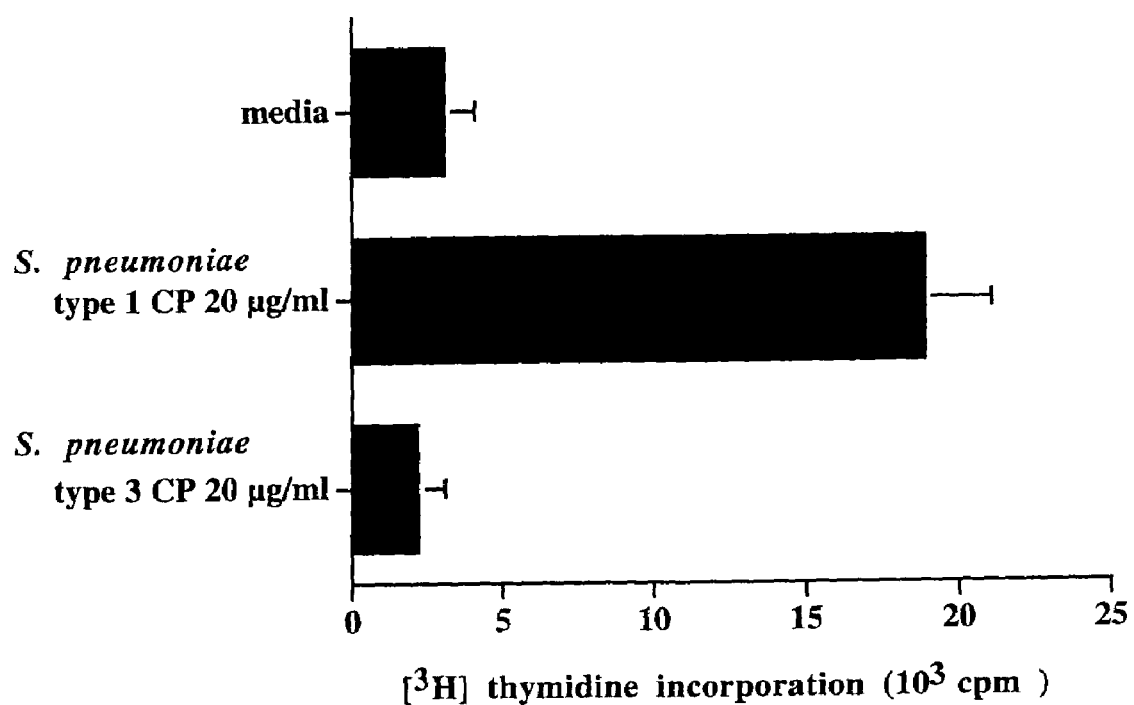
FIG. 5. Comparison of T cell proliferation by the type I CP compared with the type 3 CP. The type 3 CP consists of a repeating unit of glucose and glucuronic acid and did not elicit a T cell response in these assays.

The type 1 CP elicited a potent dose-dependent T cell response that peaked after 6 days of culture and was typically 60–70% of the PS A response in this assay. N-acetylation of type 1 CP, confirmed by NMR spectroscopy, abrogated T cell proliferation (FIG. 4). *S. pneumoniae* type 3 CP, with a disaccharide repeating unit of glucose and glucuronic acid, did not elicit a T cell response in these assays (FIG. 5).

Example 4

Characterization of Zwitterionic Polymer Charge Motif Responsible for T Cell Activation In order to demonstrate the role of the zwitterionic charge motif in T cell activation, a dipeptide repeating unit was synthesized to mimic the repeating unit structure of PS A. For this purpose, different repeating unit sizes of lysine (K) and aspartic acid (D), $(K-D)_n$, were synthesized and tested for their ability to stimulate CD4+ T cells.

Peptides $(K-D)_n$ were synthesized on a Rainin Symphony peptide synthesizer with 4-alkoxybenzyl alcohol (PAC) resins (PerSeptive Biosystems, Inc., Framingham, Mass.) using Fmoc chemistry. Amino acids were activated with 2-(1H-benzotriazole-1-yl)-1,1,3,3 tetramethyluronium hexafluorophosphate (HBTU) for coupling. The peptides prepared were analyzed by matrix-assisted laser desorption ionization-time-of-flight (MALDI-TOF) mass spectrometry and nuclear magnetic resonance (NMR) spectroscopy. Mass spectra were acquired on a Voyager MALDI-TOF mass spectrometer. Proton NMR spectra were acquired on a Brucker AMX500 instrument with proton frequency of 500 MHz. Both analyses confirmed that the peptides were the expected structures.

Following the T cell proliferation assay of Example 2, K-D peptides (20 µg/ml) of varying size were assessed for their ability to stimulate T cell activation 6 days post-incubation. The *S. pneumoniae* type 1 CP (20 µg/ml) was included as a positive control.

Figure 6:
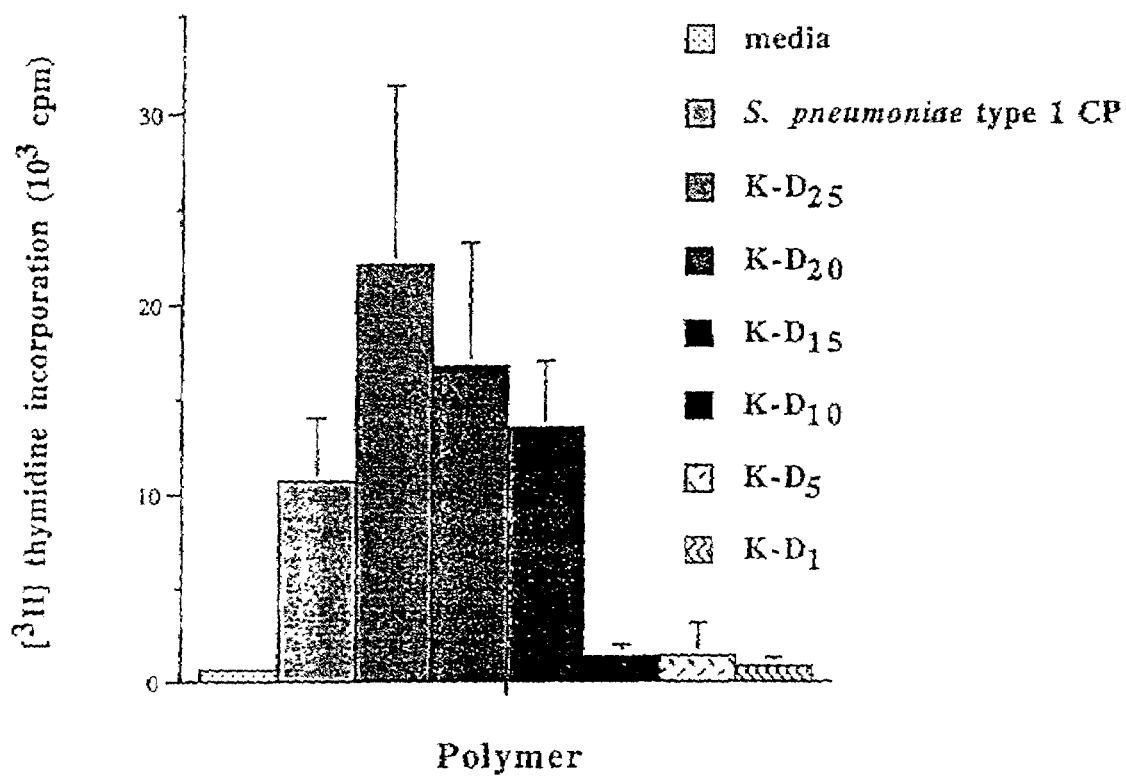
FIG. 6. Effect of repeating unit size on T cell proliferation. K-D peptides (20 µg/ml) of varying size were assessed for their ability to stimulate T cell activation 6 days post-incubation. Culture of polymers consisting of 15, 20, or 25 repeats with T cells and APCs resulted in T cell proliferation. Incubation with peptides with 1, 5 or 10 repeats did not stimulate T cell activation. The *S. pneumoniae* type I CP (20 µg/ml) was included as a positive control.

K-D peptides consisting of 15, 20 or 25 repeating units each stimulated T cell activation in vitro (FIG. 6). The response was less in peptides of 10 repeats. Peptides consisting of less than 10 repeating units (1 and 5 repeats) did not stimulate T cell activation. A control peptide, poly-L- lysine, also did not stimulate T cell proliferation. These data clearly indicate that zwitterionic repeating unit polymers other than polysaccharides stimulate T cell activation and that this activity depends on the repeating unit size of the polymer.

Example 5

Zwitterionic Polypeptides Protect Against Abscess Formation

This example addresses whether zwitterionic $(K-D)_n$ peptides could protect animals against abscess formation in vivo, using the abdominal sepsis model in Example 1. Animals were administered 50 or 5 µg of the 25 repeating unit K-D peptide $(K-D)_{25}$ and challenged with *B. fragilis*. The results are shown in Table 1, Experiment A. Treatment with the higher dose of $(K-D)_{25}$ yielded significant protection in animals compared with the saline-treated control group (17% compared with 78%, respectively, $p<0.0005$). However, treatment with the lower dose of the peptide failed to protect. The zwitterionic polysaccharide *S. pneumoniae* type I CP yielded significant protection of animals at the 50 µg dose, but not at the 5 µg dose. Administration of poly-L-lysine at the higher dose did not protect against abscess formation. Finally, treatment of animals with $(K-D)_{25}$ protected animals against intraabdominal abscess formation by the important pathogen *S. aureus* (Table 1, Experiment B). Animals treated with saline and challenged with *S. aureus* had an 80% abscess rate, while treatment with 50 µg of $(K-D)_{25}$ reduced abscess formation to 20% ($p<0.02$). These data correlate with our previous studies demonstrating that treatment of animals with PS A prevents abscesses induced by a broad range of intestinal organisms commonly associated with intraabdominal sepsis in humans. Tzianabos, A O et al. *J Clin Invest* 96:2727 (1995).

The effect of the peptide repeating unit size on protection was examined. Animals were treated according to the regimen described above with a 50 µg/dose of each repeating unit size (Table 2). Treatment with the 15, 20 or 25 repeating unit peptide resulted in a significant level of protection. However, treatment with peptide repeating units of less than 10 repeats did not yield significant protection compared with animals treated with saline. In fact, for peptides less than 10 repeats, the level of protection diminished as the repeating unit size decreased. The correlation of the T cell proliferation data with the in vivo protection studies strongly indicates that there is an optimal repeating unit size that is critical for these activities.

TABLE 1

Protection against abscess formation by the peptide $(K-D)_{25}$. Dipeptide repeating units were synthesized as described. Animals were treated with 50 µg of the appropriate polymer via the subcutaneous route at −24, 0, and +24 h relative to challenge as previously described. Tzianabos, AO et al. J Clin Invest 96:2727 (1995). Animals were challenged with *B. fragilis* ($1 \times 10^8$ cfu/rat) or *S. aureus* PS 80 ($1 \times 10^7$ cfu/rat) and examined for the formation of intraabdominal abscesses six days later.

| Treatment | Dose (µg) | Abscess formation (%) No. animals with abscess/total | p value[1] |
|---|---|---|---|
| Experiment A: Protection against *B. fragilis* | | | |
| saline | — | 14/18 (78%) | — |
| $(K-D)_{25}$ | 50 | 3/18 (17%) | <0.0005 |
| $(K-D)_{25}$ | 5 | 10/17 (59%) | >0.05 |
| *S. pneumoniae* type 1 CP | 50 | 4/20 (20%) | <0.0001 |
| *S. pneumoniae* type 1 CP | 5 | 7/16 (44%) | >0.05 |
| poly-L-lysine | 50 | 8/10 (80%) | >0.05 |
| Experiment B: Protection against *S. aureus* | | | |
| saline | — | 8/10 (80%) | — |
| $(K-D)_{25}$ | 50 | 2/10 (20%) | <0.02 |

[1]compared with saline treated control. Comparison of abscess formation between groups of animals was made by Chi squared analysis (InStat, GraphPad Software, Inc., San Diego, CA).

TABLE 2

Protection against abscess formation by different repeating unit sizes of $(K-D)_n$. Animals were treated with 50 µg of the appropriate polymer via the subcutaneous route at −24, 0, and +24 h relative to challenge as previously described. Tzianabos, AO et al. J Clin Invest 96:2727 (1995). Animals were challenged with *B. fragilis* ($1 \times 10^8$ cfu/rat) and examined for the formation of intraabdominal abscesses six days later.

| Treatment | Repeating unit size | Abscess formation (%) No. animals with abscess/total | p value[1] |
|---|---|---|---|
| saline | — | 7/7 (100%) | — |
| $(K-D)_{25}$ | 25 | 2/9 (22%) | 0.003 |
| $(K-D)_{20}$ | 20 | 1/10 (10%) | 0.0004 |
| $(K-D)_{15}$ | 15 | 5/10 (50%) | 0.04 |
| $(K-D)_{10}$ | 10 | 6/10 (60%) | >0.05 |
| $(K-D)_{5}$ | 5 | 8/10 (80%) | >0.05 |
| $(K-D)_{1}$ | 1 | 6/7 (86%) | >0.05 |
| *S. Pneumoniae* | — | 3/10 (30%) | 0.001 |

[1]compared with saline treated control. Comparison of abscess formation between groups of animals was made by Chi-squared analysis (InStat, GraphPad Software, Inc., San Diego, CA).

Example 6

T Cell Transfer Studies in Abscess Formation

Cell transfer experiments were performed as previously described. Tzianabos, A O et al. *J Clin Invest* 96:2727 (1995). Animals were treated subcutaneously with a total of 4 doses of PS A (10 µg/dose) for one week prior to harvest of spleens. Spleens were removed from PS A-treated or saline-treated rats, counted using a Coulter FN counter (Coulter Electronics Inc., Hialeah, Fla.), and examined for viability by trypan blue exclusion. The preparation was enriched for T cells by passage over nylon wool columns (greater than 95% pure T cells as assessed by FACS analysis). T cells were fractionated by treatment with specific antibody for CD4+ or CD8+ T cells (Biosource International, Camarillo, Calif.) and negative selection with magnetic beads (Perseptive Diagnostics, Cambridge, Mass.) as previously described. Finberg, R W et al. *J Immunol* 149: 2055 (1992); Haregowoin, A et al. *Nature* 340:309 (1989). Confirmation of purified cell populations following magnetic bead separation was performed by FACS analysis showed that respective cell populations were >95% pure. Purified T cells were then counted and adjusted to appropriate cell number ($3\times10^6$/animal) prior to intra-cardiac transfer to animals (0.2 ml). Animals were challenged with B. fragilis inocula 24 hours after T cell transfer, and percent of animals with abscesses per group was determined 6 days later. Results are shown in Table 3.

Animals receiving unfractionated T cells from saline-treated animals developed abscesses (84% abscess rate), while only 28% of animals receiving unfractionated T cells from PS A-treated animals formed abscesses (p=0.0001). The transfer of CD4+ T cells from PS A-treated animals reduced the rate of abscess formation in recipient animals to 29% (p=0.0001), while animals receiving CD8+ T cells had a 75% abscess rate. The number of animals receiving CD8+ T cells from PS A-treated rats that developed abscesses was significantly higher than animals receiving CD4+ T cells from similarly treated animals (p<0.005).

TABLE 3

CD4+ T cells mediate protection against abscess formation by B. fragilis.

| Treatment of donor animal[1] | Transferred cell | Abscess formation No. animals with abscess/total (%) | p value[2] |
|---|---|---|---|
| saline | T cells | 21/25 (84%) | — |
| PS A | T cells | 7/25 (28%) | 0.0001 |
| | CD4+ | 7/24 (29%) | 0.0001 |
| | CD8+ | 12/16 (75%) | NS |
| | sham Ab-depleted T cells[3] | 2/10 (20%) | 0.001 |

[1]Animals were treated via the subcutaneous route with 10 µg of PS A four times prior to harvest of T cells.
[2]Compared with animals given T cells from saline-treated rats
[3]T cells incubated with isotype matched monoclonal antibody specific for rat B cell marker Example 7

Soluble Factors in the CD4+ T Cell Response to Zwitterionic Polymer Charge Motif To further characterize this protective activity, a CD4+ T cell population taken from saline- or PS A-treated animals according to Example 6 was subjected to a freeze/thaw procedure to lyse cells or fixed with 1% paraformaldehyde. Lysates of T cells were generated by subjecting enriched T cell populations to a freeze/thaw cycle three times. Cell debris was centrifuged (3,000×g) and the remaining lysate used (equivalent of 3×10$^6$ cells/animal) for in vivo T cell transfer studies. The subsequent cell lysate or fixed cell population was transferred to naive recipient animals 24 h prior to challenge with B. fragilis as described in Example 6. Results are shown in Table 4.

Animals given untreated, lysed, or fixed cells from saline-treated rats developed abscesses (72%, 90%, and 75%, respectively). Transfer of intact CD4+ T cells or lysates of CD4+ T cell from PS A-treated rats conferred protection in naive T cell recipients (22% and 17% abscess rate, respectively). However, fixation of the CD4+ T cells taken from PS A-treated animals abrogated the protective activity yielding an 88% abscess rate compared with 75% in animals given fixed saline-treated CD4+ T cells.

TABLE 4

Effect of treatment of transferred CD4+ T cells on intraabdominal abscess formation.

| Treatment of animal donor[1] | Treatment of transferred CD4+ T cell[2] | Abscess formation No. animals with abscess/total (%) | p value[3] |
|---|---|---|---|
| saline | untreated | 18/25 (72%) | — |
| | lysed | 17/19 (90%) | — |
| | fixed | 15/20 (75%) | — |
| PS A | untreated | 6/27 (22%) | <0.001 |
| | lysed | 3/18 (17%) | <0.0001 |
| | fixed | 14/16 (88%) | NS[4] |

[1]Animals were treated subcutaneously with saline or PS A (10 µg) four times prior to harvest of T cells.
[2]3 × 10$^6$ T cells or T cell lysates derived from this number of cells were transferred to each animal.
[3]Compared with animals give similarly treated T cells from saline-treated rats
[4]NS = not significant Example 8

Cytokine mRNA Expression by T Cells from PS A-Treated Animals

Animals were treated with PS A as described in Example 6 for T cell transfer experiments and RT-PCR analyses performed on purified splenic T cells. Total cellular RNA was collected from the purified T cells using a RNeasy Mini Kit (Qiagen, Santa Clarita, Calif.). Briefly, 1×10$^7$ cells were lysed, homogenized by repetitive passage through a 20 gauge needle, and applied to an RNA affinity column. Residual DNA was digested with DNase I (Gibco BRL, Rockville, Md.) and the RNeasy Kit was used to purify the RNA. After RNA integrity was confirmed by electrophoresis on a 1% (w/v) agarose gel, reverse transcription (RT) was performed using the Superscript RT-PCR Kit (Gibco BRL, Rockville. MD). RNA in 10 µg aliquots was primed with oligo (dT) and RT was performed according to manufacturer's instructions. Resulting cDNA was treated with RNase (Gibco BRL, Rockville, Md.) and PCR was performed in a 50 µl reaction volume containing 1.5 mM MgCl2, 20 mM Tris-HCl, 0.2 mM dNTPs, 0.1% Triton X-100, 2.5 U Taq polymerase, 200 ng of cDNA, and 200 ng of each primer. Step down PCR, a simplified version of touch down PCR, was implemented to reduce the formation of non-specific products. Hecker, K H et al. Biotechniques 20:478 (1996). A hot start was performed at 94° C. for 4 min. Cycling conditions consisted of 1 min denaturation at 94° C. 2 min annealing with 3 cycles at each annealing temperature (67° C., 64° C., 61° C., 58° C., 55° C. and 51° C.), and extension 3 min at 72° C. An additional 20 cycles were done with an annealing temperature of 52° C., for a total of 38 cycles. For IL-4. PCR was performed at an annealing temperature of 58° C. for 35 cycles. Intron-spanning primers were designed using the GeneStar program:

| β-Actin sense | 5'-CCAACCGTGAAAAGATGACCC-3' | SEQ ID NO: 1 |
|---|---|---|
| β-Actin antisense | 5'-TCGTACTCCTGCTTGCTGATC C-3' | SEQ ID NO: 2 |
| IL-2 sense | 5'-ACGCTTGTCCTCCTTGTCAAC-3' | SEQ ID NO: 3 |
| IL-2 antisense | 5'-CCATCTCCTCAGAAATTCCACC-3' | SEQ ID NO: 4 |
| IL-4 sense | 5'-GCTGTCACCCTGTTCTGCTTTC-3' | SEQ ID NO: 5 |

-continued

| | | |
|---|---|---|
| IL-4 antisense | 5'-TCATTAACGGTGCAGCTTCTC-3' | SEQ ID NO: 6 |
| IL-10 sense | 5'-ACAATAACTGCACCCACTTCC-3' | SEQ ID NO: 7 |
| IL-10 antisense | 5'-AAATCATTCTTCACCTGCTCC-3' | SEQ ID NO: 8 |
| IFN-γ sense | 5'-CCATCAGCAACAACATAAGTGTC-3' | SEQ ID NO: 9 |
| IFN-γ antisense | 5'-ACTCCTTTTCCGCTTCCTTAG-3' | SEQ ID NO: 10 |

Negative controls without cDNA were amplified for every PCR experiment. The authenticity of the primers was determined in specific IL-2, IFN-γ, IL-4 and IL-10 T cell stimulation assays. The cDNA products were visualized by electrophoresis on 1.5% agarose gels following staining with ethidium bromide. Results are shown in FIG. 7.

Elevated mRNA levels of the Th1 cytokines IL-2 and IFN-γ were detected from T cells taken from PS A-treated animals. In addition, transcript for the Th2 cytokine IL-10 was also observed. The presence of transcript for IL-4 was not noted from these T cell preparations. Analysis of T cells from saline-treated animals did not demonstrate mRNA transcript for IL-2, IFN-γ, IL-4 or IL-10.

Example 9

Neutralization of Protection by Cytokine-Specific Antibodies

To assess the role of cytokines in the transfer of protection, T cell lysates according to Example 7 were treated with antibodies to neutralize specific cytokines. For these antibody neutralization studies, the equivalent of $3 \times 10^6$ cells/animal was mixed with 50 μg of the appropriate antibody for 30 min at room temperature and administered via the intracardiac route. Polyclonal antibody specific for IL-2 (BioSource International, Camarillo, Calif.) and monoclonal antibodies specific for IL-10 and IFN-γ (PharMingen, San Diego, Calif.) were used for neutralization experiments. Isotype matched rat antibodies were used as negative controls. Results are shown in Table 5.

Addition of antibody specific for IFN-γ or IL-10 to T cell lysates taken from PS A-treated animals did not neutralize the transfer of protection against abscess formation. Mixing of these cytokine-specific antibodies with T cell lysates from saline-treated animals did not alter the ability of recipient animals to form abscesses following challenge. However, mixing IL-2-specific antibodies with T cell lysates from PS A-treated animals abrogated the protective activity. Transfer of PS A lysates mixed with IL-2-specific antibody resulted in a 76% abscess rate compared with a 27% rate of abscess formation in animals receiving PS A lysates mixed with an isotype matched control antibody (p<0.0005).

TABLE 5

Effect of cytokine-specific antibody treatment of transferred T cell lysates.

| T cell lysate Transfer[1] | Ab treatment | Abscess formation No. animals with abscess/total (%) | p value[2] |
|---|---|---|---|
| saline | sham Ab[3] | 7/10 (70%) | — |
| saline | anti-IL-10 | 7/9 (78%) | — |
| saline | anti-IFN-γ | 7/9 (78%) | — |

TABLE 5-continued

Effect of cytokine-specific antibody treatment of transferred T cell lysates.

| T cell lysate Transfer[1] | Ab treatment | Abscess formation No. animals with abscess/total (%) | p value[2] |
|---|---|---|---|
| saline | anti-IL-2 | 13/18 (72%) | — |
| PS A | sham Ab | 0/8 (0%) | <0.005 |
| PS A | anti-IL-10 | 1/9 (11%) | <0.05 |
| PS A | anti-IFN-γ | 1/10 (10%) | <0.01 |
| PS A | anti-IL-2 | 16/21 (76%) | <0.0005[4] |

[1]Animals were treated subcutaneously with saline or PS A (10 μg) four times prior to harvest of T cells. The equivalent of $4 \times 10^6$ T cells was transferred to each animal.
[2]compared with respective saline control group
[3]animals were treated with isotype matched control Ab
[4]compared with PS A lysate mixed with sham Ab Example 10

IL-2-Mediated Protection Against Abscess Formation

In order to demonstrate the role of IL-2 in conferring protection against abscess formation, we performed experiments in which recombinant IL-2 was administered to animals via the intracardiac route at the time of intraperitoneal challenge with B. fragilis. Results are shown in Table 6.

Protection by IL-2 occurred in a dose-dependent manner. Animals receiving 1000 or 100 pg of IL-2 had significantly fewer abscesses than those receiving saline (p<0.002), while a dose of 10 pg failed to confer a significant level of protection. Animals receiving 100 pg of IL-2 had a significantly lower rate of abscesses compared with animals receiving saline (Table 6, Experiment A, 27% versus 70%, p<0.005). Animals receiving IL-4 at this dose were not protected against abscess formation (75% abscess rate).

TABLE 6

Protection against abscess formation[1] by recombinant IL-2.

| | Treatment | Abscess formation No. animals with abscess/total (%) | p value[2] |
|---|---|---|---|
| Experiment A | saline | 21/30 (70%) | — |
| | IL-2 (100 pg) | 10/37 (27%) | <0.005 |
| Experiment B | saline | 9/9 (100%) | — |
| | IL-2 (1000 pg) | 2/8 (25%) | 0.002 |
| | IL-2 (100 pg) | 1/8 (12.5%) | <0.001 |
| | IL-2 (10 pg) | 6/10 (60%) | NS[3] |

[1]animals were challenged with $10^8$ cfu/animal B. fragilis
[2]compared with saline-treated control groups
[3]not significant Example 11

IL-10-Mediated Protection Against Abscess Formation

In order to examine further the role of IL-10 in the abscess model, male Wistar rats (150 g) were treated with recombinant IL-10, anti-IL-10, or isotype antibody control beginning on the day of challenge with $1 \times 10^8$ cfu B. fragilils. Further comparison was made using a group treated with Streptococcus pneumoniae type I CP alone or together with anti-IL-10. Animals were sacrificed and examined six days after challenge. Results are shown in Table 7.

All rats treated with isotype control antibody developed abscesses, while rats treated with type I CP or recombinant IL-10 were protected from abscess formation (p<0.0001 in both these groups). Addition of anti-IL-10, either alone or in combination with type I CP resulted in no significant protection against abscess formation. The protective effect of recombinant IL-10 and the abrogation by anti-IL-10 of the protective effect conferred by type 1 CP together demonstrate an association between treatment with zwitterionic polysaccharide of the invention and IL-10-mediated protection against abscess formation.

TABLE 7

Protection against abscess formation[1] by IL-10.

| Treatment | Dose (μg) | Abscess formation (%) No. animals with abscess/total | p value[2] |
|---|---|---|---|
| isotype-matched antibody control[3] | 0.2 | 16/16 (100%) | — |
| recombinant IL-10[3] | 0.2 | 2/16 (13%) | <0.0001 |
| S. pneumoniae type 1 CP[4] | 20 | 1/16 (6%) | <0.0001 |
| anti-IL-10[3] | 0.2 | 13/16 (81%) | >0.05 |
| S. pneumoniae type 1 CP[4] and anti-IL-10[3] | 20 0.2 | 13/16 (81%) | >0.05 |

[1]animals were challenged with $10^8$ cfu/animal B. fragilis.
[2]compared with isotype-matched antibody control, calculated by Fisher's exact test.
[3]administered i.p. at 0, 24, 48, and 72 hours relative to challenge.
[4]administered subcutaneously at −24, 0, and 24 hours relative to challenge.

Example 12

IgG Antibody Suppression Induced by PS A Treatment

SVJ mice were treated on day 0 with 50 μg of PS A via the intraperitoneal route and 2 μg of a conjugate vaccine containing type III group B streptococcus polysaccharide and tetanus toxoid. Controls received saline in place of PS A. A booster dose of conjugate vaccine was given 21 days later and animals were bled at days 38 and 56 post-vaccination. Antigen-specific IgG levels were assayed by sandwich ELISA, using specific antigen as the capture agent. Results are shown in FIG. 8.

ELISA testing of antibody levels showed that the levels of IgG specific for the type III polysaccharide in PS A-treated animals were suppressed compared to saline-treated animals. In addition, levels of IgG specific for tetanus toxoid in PS A-treated animals were also lower compared to saline-treated animals. PS A treatment thus suppressed IgG response to both polysaccharide and peptide antigens.

Example 13

Figure 9:
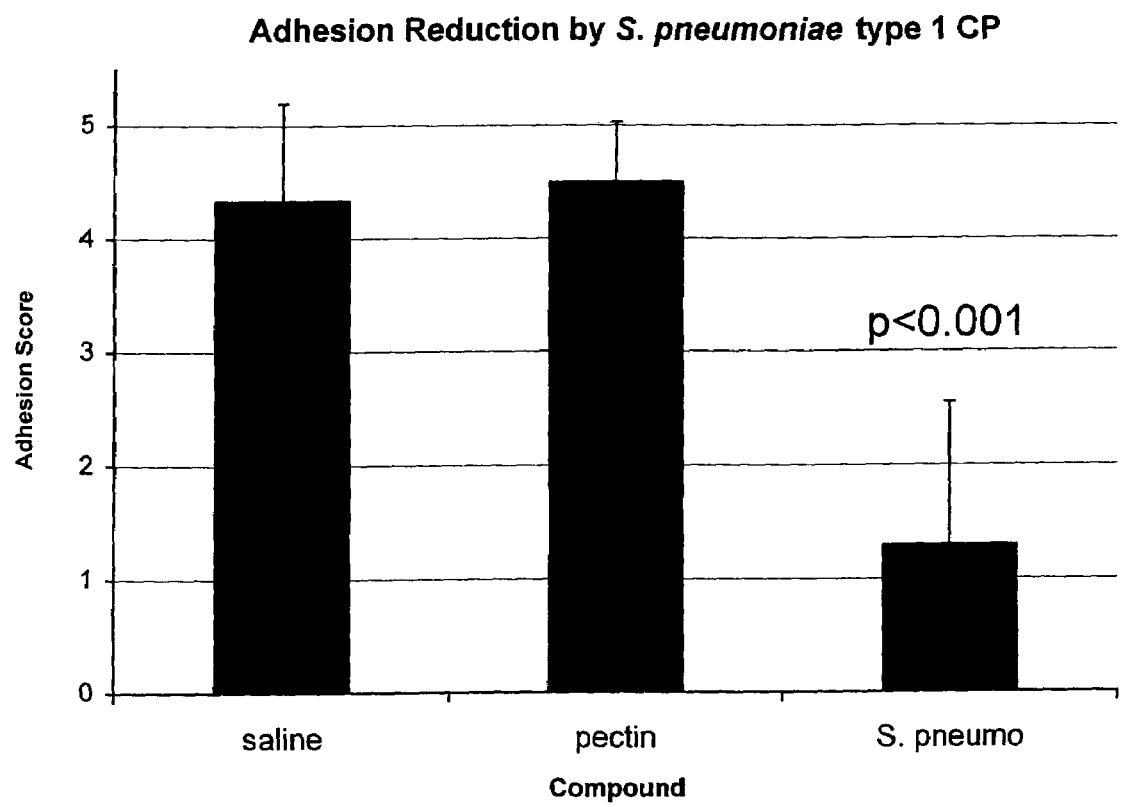
FIG. 9. Adhesion prevention by zwitterionic polysaccharide (Zps). Ten rats in each of three groups were treated with saline, pectin, or *S. pneumoniae* type 1 CP (100 micrograms per dose) at 24 hours before, on the day of, and 24 hours following cecal abrasion. Sterilized rat cecal contents (0.5 ml) were introduced into the peritoneal cavity prior to wound closure. Animals were sacrificed six days following the procedure and adhesions were scored on a scale from 0 (no adhesions) to 5 (very thick vascularized adhesions or more than one planar adhesion). Rats treated with capsular polysaccharide had significantly lower adhesion scores than rats receiving pectin ($p<0.001$).

Postoperative Surgical Adhesion Suppression by Streptococcus pneumoniae Type I CP Rats (10 per group) were treated with saline (100 μl), pectin (polygalacturonic acid, 100 μg in 100 μl saline), or the Streptococcus pneumoniae type 1 CP (a trisaccharide repeating unit with two galacturonic acid residues and a 2-acetamido-4-amino-2,4,6-trideoxygalactose, 80 kDa, 100 μg in 100 μl saline) subcutaneously at −24 h, 0 h, and +24 h relative to surgical manipulation. Adhesions were induced as previously described with some modification. Kennedy, R et al. Surgery 120:866 (1996). Briefly, a 3 cm midline incision was made into the abdominal cavity and the cecum exposed. The cecum was abraded with surgical gauze until punctate hemorrhages were visible. The cecum was inserted into the peritoneal cavity and the apposing abdominal wall abraded in a similar manner. Following this procedure, sterilized rat cecal contents (0.5 ml) was added to the peritoneal cavity as previously described. Onderdonk, A B et al. *J Clin Invest* 69:9 (1982). The wound was closed with 4.0 silk sutures. Animals were sacrificed six days later and examined for the formation of adhesions. Adhesions were scored as previously described on a scale of 0 to 5 as follows: 0, no adhesions; 1, thin filmy adhesion; 2, more than one thin adhesion; 3, thick adhesion with focal point; 4, thick adhesion with planar attachment; and 5, very thick vascularized adhesions or more than one planar adhesion. Kennedy, R et al. *Surgery* 120:866 (1996). Results are shown in FIG. 9.

Rats treated with type I CP had significantly lower adhesion scores than pectin-treated animals (p<0.001 by unpaired t test). These data show that parenteral administration of a zwitterionic polysaccharide (Zps) that possesses both positively and negatively charged groups significantly reduces adhesion formation compared with animals treated with a polysaccharide that has only negatively charged groups (pectin).

Example 14

T Cell Transfer Studies in Adhesion Formation

Animals were treated subcutaneously with a total of 4 doses of Streptococcus pneumoniae type 1 CP (50 μg/dose) for one week prior to harvest of spleens, analogous to Example 6. T cells isolated from saline or polysaccharide treated animals were fractionated, counted, and transferred via the intracardiac route 24 hours prior to the induction of adhesions following the method of Example 13. Animals were sacrificed and scored for adhesions (0–5) six days later. Results are shown in FIG. 10.

Adhesion scores in animals receiving CD4+ T cells from donors previously treated with S. pneumoniae type I CP were reduced by 50 percent compared to animals receiving T cells from saline-treated controls (p<0.02).

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

All references, patents and patent publications that are recited in this application are incorporated in their entirety herein by reference.

We claim:

1. A pharmaceutical composition comprising:
an isolated polypeptide of less than 50 kilodaltons consisting of identical repeating units, each unit having a charge motif composed of a positively charged free amino moiety and a negatively charged moiety, wherein the positively charged free amino moiety and the negatively charged moiety of each charge motif are separated by at least one neutral amino acid, and wherein the positively charged free amino moiety of one of the charge motifs is separated by a distance of at least 8 amino acids from the positively charged amino moiety of another charge motif, and
a pharmaceutically acceptable carrier.

2. The composition of claim 1, wherein the positively charged free amino moiety and the negatively charged moiety of each charge motif are separated by at least five neutral amino acids.

3. The composition of claim 1, wherein the positively charged free amino moiety of one of the charge motifs is separated by a distance of at least 27 amino acids from the positively charged free amino moiety of another charge motif.

4. The composition of claim 1, wherein the positively charged free amino moiety of one of the charge motifs is separated by a distance of at least 37 amino acids from the positively charged free amino moiety of another charge motif.

5. The composition of claim 1, wherein the positively charged free amino moiety of one of the charge motifs is separated by a distance of at least 47 amino acids from the positively charged free amino moiety of another charge motif.

6. The composition of claim 1, wherein the polypeptide is a synthetic polypeptide.

7. The composition of claim 1, wherein the polypeptide has at least ten modified amino acids.

* * * * *